(12) United States Patent
Berl

(10) Patent No.: US 8,927,043 B2
(45) Date of Patent: Jan. 6, 2015

(54) STABILIZED FORMULATIONS OF FATTY ACIDS

(75) Inventor: Volker Berl, Paramus, NJ (US)

(73) Assignee: Mycell Technologies, Paramus, NJ (US)

( * ) Notice: Subject to any disclaimer, the term of this patent is extended or adjusted under 35 U.S.C. 154(b) by 443 days.

(21) Appl. No.: 12/943,729

(22) Filed: Nov. 10, 2010

(65) Prior Publication Data

US 2011/0118351 A1 May 19, 2011

Related U.S. Application Data

(60) Provisional application No. 61/259,943, filed on Nov. 10, 2009.

(51) Int. Cl.
| | | |
|---|---|---|
| *A23L 2/52* | (2006.01) | |
| *A23D 7/005* | (2006.01) | |
| *C11B 5/00* | (2006.01) | |
| *A23L 1/30* | (2006.01) | |
| *A23D 9/007* | (2006.01) | |

(52) U.S. Cl.
CPC .............. *A23L 1/3008* (2013.01); *A23D 7/0053* (2013.01); *A23D 9/007* (2013.01); *A23L 2/52* (2013.01); *C11B 5/0028* (2013.01); *C11B 5/0035* (2013.01)
USPC ..................... 426/590; 426/541; 554/2; 516/9

(58) Field of Classification Search
CPC ................ A23V 2250/1882; A23V 2250/186; A23V 2250/1862; A23V 2250/1868; A23V 2250/1874; A23V 2250/188; A23V 2200/214; A23V 2200/238; A23V 2200/25; A23L 2/44
USPC .............................. 426/590, 541; 554/2; 516/9
See application file for complete search history.

(56) References Cited

U.S. PATENT DOCUMENTS

| | | |
|---|---|---|
| 3,065,076 A | 11/1962 | Wenner et al. |
| 4,702,799 A | 10/1987 | Tuot |
| 5,078,989 A | 1/1992 | Ando et al. |
| 5,137,723 A | 8/1992 | Yamamoto et al. |
| 6,045,826 A | 4/2000 | Borowy-Borowski |
| 6,191,172 B1 | 2/2001 | Borowy-Borowski et al. |
| 6,284,268 B1 * | 9/2001 | Mishra et al. .................. 424/455 |
| 6,344,218 B1 | 2/2002 | Dodd et al. |
| 6,632,443 B2 | 10/2003 | Borowy-Borowski et al. |
| 2003/0165572 A1 | 9/2003 | Auriou |
| 2004/0062778 A1 * | 4/2004 | Shefer et al. ................... 424/400 |
| 2006/0210622 A1 | 9/2006 | Pace et al. |
| 2006/0251685 A1 * | 11/2006 | Yu et al. ......................... 424/400 |
| 2007/0085059 A1 * | 4/2007 | Mora-Gutierrez et al. ......................... 252/400.21 |
| 2008/0058418 A1 * | 3/2008 | D'Angelo et al. ............ 514/560 |
| 2008/0206155 A1 | 8/2008 | Tamarkin et al. |
| 2008/0206159 A1 | 8/2008 | Tamarkin et al. |
| 2008/0254188 A1 * | 10/2008 | Borowy-Borowski et al. ............................ 426/590 |

FOREIGN PATENT DOCUMENTS

WO       WO 96/17626        6/1996

OTHER PUBLICATIONS

Yamamoto et al., J. Med. Chem. 2002, 45(2): 462-468.
Nihro et al., Chem. Pharm. Bull. 1991, 39: 1731-1735.
D. Martin et al., Oxidative stabilization of ultra-high omega-3 . . . Food Research International 45 (2012) 336-341.

* cited by examiner

*Primary Examiner* — Sreeni Padmanabhan
*Assistant Examiner* — Irina Neagu
(74) *Attorney, Agent, or Firm* — Sam L. Nguyen; Hamilton, DeSanctis & Cha, LLP

(57) ABSTRACT

Disclosed herein are stabilized powder and aqueous formulations comprising a substantially water insoluble lipophilic bioactive compound and a micelle-forming surfactant. In one embodiment, the formulation further comprises a water soluble reducing agent, and/or a water insoluble reducing agent, and/or a metal chelator, and/or a metal bisulfite reducing agent, or combinations thereof, wherein the formulation remains substantially clear and stable when stored at or below room temperature for a period of at least 6 months or at least 12 months; and methods for preparing these formulations.

13 Claims, No Drawings

STABILIZED FORMULATIONS OF FATTY ACIDS

RELATED APPLICATION

This application claims the benefit of U.S. Provisional Application No. 61/259,943 filed Nov. 10, 2009, which is incorporated herein by reference.

SUMMARY OF THE PRESENT APPLICATION

A need exists for novel methods of preparing stabilized formulations comprising food, beverage, pharmaceutical or nutraceutical products containing nutritional products. The following embodiments, aspects and variations thereof are exemplary and illustrative are not intended to be limiting in scope.

In one embodiment, there is provided a stable, substantially clear, water soluble formulation comprising:
a) an omega-fatty acid;
b) a solubilizing agent comprising the Formula (I):

$$Y^1\text{-}[L^1]_a\text{-}Z \qquad (I)$$

wherein:
a is 0 and 1;
$L^1$ is a linker moiety that covalently links the hydrophobic moiety Z and the hydrophilic moiety $Y^1$;
$Y^1$ is a linear or branched hydrophilic moiety comprising at least one polymeric moiety independently selected from poly(alkylene oxides) and polyalcohols or monoethers derived therefrom; and
Z is a hydrophobic moiety.

In another embodiment, the water-soluble formulation further comprises a water soluble antioxidant. In another embodiment, the water-soluble formulation further comprises a metal chelator. In another embodiment, the water-soluble formulation further comprises a water-soluble reducing agent. In yet another embodiment, the water-soluble formulation further comprises a lipophilic antioxidant. In another embodiment, the water-soluble formulation further comprises a lipophilic reducing agent, or a combination of each of the above.

In one aspect of the above formulation, the omega-fatty acid is selected from the group consisting of omega-3 fatty acids, omega-6 fatty acids, omega-9 fatty acids and omega-12 fatty acids. In another aspect, the omega-fatty acid is selected from the group consisting of α-linolenic acid (ALA), stearidonic acid, eicosatetraenoic acid, eicosapentaenoic acid (EPA), docosapentaenoic acid, docosahexaenoic acid (DHA), linoleic acid, gamma-linolenic acid, eicosadienoic acid, dihomo-gamma-linolenic acid, arachidonic acid, docosadienoic acid, adrenic acid, docosapentaenoic acid, oleic acid, eicosenoic acid, mead acid, erucic acid and nervonic acid. In another aspect of the formulation, the solubilizing agent comprises the Formula (I), wherein:
Z is selected from the group consisting of sterols, tocopherols, tocotrienol and omega-fatty acids and derivatives or homologues thereof;
$L^1$ is selected from a single bond, substituted or unsubstituted alkylene, substituted or unsubstituted heteroalkylene, substituted or unsubstituted arylene, substituted or unsubstituted heteroarylene and substituted or unsubstituted heterocycloalkylene; and $Y^1$ is a linear or branched hydrophilic moiety including at least one polymeric moiety, wherein each polymeric moiety is a member independently selected from poly (alkylene oxides), polyalcohols, and polyalcohol monoethers, and polysaccharides.

In another aspect of the water-soluble formulation: $Y^1$ is selected from the group consisting of poly(alkylene oxides) and monoethers derived therefrom, polyalcohols, polysaccharides, polyamino acids, polyphosphoric acids, polyamines and derivatives thereof; and $L^1$ is selected from the group consisting of a linear or branched $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$ or $C_{25}$-$C_{30}$ alkylene chain, optionally incorporating at least one functional group selected from the group consisting of ether, thioether, ester, carboxamide, sulfonamide, carbonate and urea groups. In one variation, the solubilizing agent is selected from the group consisting of solubilizing agents having a hydrophilic-lipophilic balance (HLB) of 8-18, HLB of 7-9 and HLB of 8-12, HLB of 13-15, TPGS (polyoxyethanyl-a-tocopheryl succinate) and combinations thereof. In another aspect, the solubilizing agent is TPGS (polyoxyethanyl-a-tocopheryl succinate) or TPGS-1000 (D-alpha-tocopheryl polyethylene glycol 1000 succinate), wherein the tocopheryl is the natural tocopherol isomer or the un-natural tocopherol isomer. In another aspect, the water soluble reducing agent is L-ascorbic acid-6-palmitate. In another embodiment, the metal chelator is ethylenediaminetetraacetic acid. In another embodiment, the reducing agent is sodium bisulfite.

In another embodiment, there is provided a method for stabilizing a substantially water insoluble lipophilic bioactive compound in an aqueous solution comprising contacting the lipophilic bioactive compound with a composition comprising a micelle-forming surfactant, a water soluble reducing agent, and a metal chelator in water, at an elevated temperature, and for a sufficient period of time to dissolve the lipophilic bioactive compound. In one aspect, the lipophilic bioactive compound is an omega-fatty acid. In another aspect, the micelle-forming surfactant is TPGS (polyoxyethanyl-atocopheryl succinate). In a particular variation, the surfactant is TPGS-1000. In one variation, the metal chelator ethylenediaminetetraacetic acid. In another variation, the method further comprises contacting the aqueous solution with a metal bisulfite reducing agent.

In one embodiment, there is provided a stabilized aqueous formulation comprising a substantially water insoluble lipophilic bioactive compound, a micelle-forming surfactant, a water soluble reducing agent, a metal chelator and a reducing agent, wherein the formulation remains substantially clear and stable when stored at or below room temperature for a period of at least 6 months or at least 12 months. In one aspect of the formulation, the lipophilic bioactive compound is an omega-fatty acid. In another aspect, the omega-fatty acid is an omega-3-fatty acid. In another aspect, the omega-fatty acid is an omega-3-, omega-6- and omega-9-fatty acid $C_1$-$C_{10}$ alkyl esters, $C_1$-$C_5$ alkyl esters, $C_1$-$C_3$ alkyl esters or $C_2$-$C_5$ alkyl esters. In one aspect, the omega-fatty acids is an omega-3-, omega-6- and omega-9-fatty acid ethyl ester. Accordingly, in another embodiment, there is provided a stabilized food, beverage, pharmaceutical or nutraceutical product comprising the aqueous formulation of the above.

In addition to the exemplary embodiments, aspects and variations described above, further embodiments, aspects and variations will become apparent by reference to the drawings and figures and by examination of the following descriptions.

DETAILED DESCRIPTION OF THE PRESENT APPLICATION

DEFINITIONS:

Unless specifically noted otherwise herein, the definitions of the terms used are standard definitions used in the art of organic synthesis and pharmaceutical sciences. Exemplary embodiments, aspects and variations are illustrative in the figures and drawings, and it is intended that the embodiments, aspects and variations, and the figures and drawings disclosed herein are to be considered illustrative and not limiting.

Definitions

The term "vitamin C derivative" as used herein means any compound that releases ascorbic acid (vitamin C) in vivo or in vitro, as well as solvates, hydrates and salts thereof. The term also includes vitamin C analogs wherein one or more of the hydroxyl groups of vitamin C are substituted with another moiety and wherein the vitamin C analog essentially retains the stabilizing activity of vitamin C in vitro or in vivo.

The term "monoterpene" as used herein, refers to a compound having a 10-carbon skeleton with non-linear branches. A monoterpene refers to a compound with two isoprene units connected in a head-to-tail manner. The term "monoterpene" is also intended to include "monoterpenoid", which refers to a monoterpene-like substance and may be used loosely herein to refer collectively to monoterpenoid derivatives as well as monoterpenoid analogs. Monoterpenoids can therefore include monoterpenes, alcohols, ketones, aldehydes, ethers, acids, hydrocarbons without an oxygen functional group, and so forth.

As used herein, the term "phospholipid" is recognized in the art, and refers to phosphatidyl glycerol, phosphatidyl inositol, phosphatidyl serine, phosphatidyl choline, phosphatidyl ethanolamine, as well as phosphatidic acids, ceramides, cerebrosides, sphingomyelins and cardiolipins.

As used herein, the term "solubilizing agent" is used interchangeably with the term "surfactant". In one embodiment, the solubilizing agent is a nonionic, amphiphilic molecule, wherein the term amphiphilic means that the molecule includes at least one hydrophobic (e.g., lipid-soluble) moiety, such as a moiety derived from a tocopherol, a sterol, or a quinone (or derived hydroquinone, such as in the case of ubiquinone and ubiquinol) and at least one hydrophilic (e.g., water-soluble) moiety, such as polyethylene glycol or a simple sugar, carbohydrate or a carbohydrate drivative.

As used herein, the terms "stabilizer", and "antioxidant", are recognized in the art and refer to synthetic or natural substances that prevent or delay the oxidative or free radical or photo induced deterioration of a compound, and combinations thereof. Exemplary stabilizers include tocopherols, flavonoids, catechins, superoxide dismutase, lecithin, gamma oryzanol; vitamins, such as vitamins A, C (ascorbic acid) and E (tocopherol and tocopherol homologues and isomers, especially alpha and gamma- and delta-tocopherol) and beta-carotene (or related carrotenoids); natural components such as camosol, carnosic acid and rosmanol found in rosemary and hawthorn extract, proanthocyanidins such as those found in grape seed or pine bark extract, and green tea extract. In one variation, the vitamin E includes all 8-isomers (all-rac-alpha-tocopherol), and also include d,l-tocopherol or d,l-tocopherol acetate. In one variation, the vitamin E is the d,d,d-alpha form of vitamin E (also known as natural 2R,4R',8R'-alpha-tocopherol). In another variation, the vitamin E includes natural, synthetic and semi-synthetic compositions and combinations thereof.

The term "reducing agent" is any compound capable of reducing a compound of the present application to its reduced form. "Reducing agent" includes lipophilic (e.g., lipid-soluble) reducing agents. In one example, the lipid-soluble reducing agent incorporates a hydrophobic moiety, such as a substituted or unsubstituted carbon chain (e.g., a carbon chain consisting of at least 10 carbon atoms). "Reducing agent" also includes hydrophilic (e.g., water-soluble) reducing agents. In one variation, the reducing agent that may be employed in the formulation is ubiquinol.

In one example, the reducing agent is a "water-soluble reducing agent" when the reducing agent dissolves in water (e.g., at ambient temperature) to produce a clear solution, as opposed to a visibly cloudy, hazy or otherwise inhomogeneous mixture, or even a two phase system. In one example, the reducing agent is a "water-soluble reducing agent" when it includes at least one (e.g., at least two) hydroxyl group(s) and does not include a large hydrophobic moiety (e.g., a substituted or unsubstituted linear carbon chain consisting of more than 10, 11, 12, 13, 14, 15, 16, 17, 18, 19 or 20 carbon atoms). In another example, the reducing agent is a "water-soluble reducing agent" when it includes at least one (e.g., at least two) hydroxyl group(s) and includes a substituted or unsubstituted linear carbon chain consisting of not more 6, 8, 10, 11, 12, 13, 14 or 15 carbon atoms. An exemplary water-soluble reducing agent is ascorbic acid. The term "water-soluble reducing agent" also includes mixtures of vitamin C with a lipophilic bioactive molecule of the present application. Water-soluble reducing agents can be derivatized to afford an essentially lipid-soluble reducing agent (pro-reducing agent). For example, the water-soluble reducing agent is derivatized with a fatty acid to give, e.g., a fatty acid ester. An exemplary lipid-soluble reducing agent is ascorbic acid-palmitate.

The term "water-soluble" when referring to a formulation or compositions of the present application, means that the formulation when added to an aqueous medium (e.g., water, original beverage) dissolves in the aqueous medium to produce a solution that is essentially clear. In one example, the formulation dissolves in the aqueous medium without heating the resulting mixture above ambient temperature (e.g., 25° C.). The term "essentially clear" is defined herein.

The term "aqueous formulation" refers to a formulation of the present application including at least about 5% (w/w) water. In one example, an aqueous formulation includes at least about 10%, at least about 20%, at least about 30% at least about 40% or at least about 50% (w/w) of water.

The term "bioactive" refers to compounds and compositions of the present application. For example, a bioactive molecule is any compound having in vivo and/or in vitro biological activity. In one embodiment, the bioactive or bioactive molecule is a fatty acids, such as omega-fatty acids (or used interchangeably with omega-fatty acid). Bioactive molecules or compositions also include those, which are suspected in the art to have biological activity (e.g., to have a positive effect on human health and/or nutrition). In one example, the biological activity is a desirable biological activity but can be accompanied by undesirable side-effects. Compounds with biological activity include pharmaceuticals, neutraceuticals and dietary supplements.

The terms "omega-fatty acid(s)" and "omega-3-fatty acid(s)" are used interchangeably to mean the same composition, as known in the art, and include, for example, omega-3-, omega-6- and omega-9-fatty acids. Such omega-fatty acids are the naturally occurring plant derived oils (including algae derived oils) or fish oils that are the mono- di- and triglyceride derivatives of omega-fatty acids. Non-naturally occurring (or non-natural) omega-fatty acids or omega-3-fatty acids include the non-glyceride esters of the omega-3- fatty acids. Such non-naturally occurring omega-fatty acids include the ethyl esters of omega-fatty acids that are, for example, the omega-3-, omega-6- and omega-9-fatty acids ethyl esters, and are also referred to as fatty acids ethyl esters (FAEE) or EEs fish oil. In certain embodiments of the present application, the non-naturally occurring omega-fatty acids used in the compositions of the present application comprise the $C_1$-$C_{10}$ alkyl esters, the $C_1$-$C_5$ alkyl esters, the $C_1$-$C_3$ alkyl esters or the $C_2$-$C_5$ alkyl esters. Further, in certain embodiments of the present application, the omega-fatty acids used in the composition of the present application are a mixture of the triglycerides of the omega-fatty acids and (i.e., mixed with) the omega-fatty acid esters, as defined herein. Accordingly, as used herein, unless otherwise noted, the term "omega-fatty acids" as used in each aspects, variations and embodiments of the formulations of the present application include the natural omega-fatty acids, the non-natural omega-fatty acids, and their esters, and mixtures thereof, as defined herein.

The term "pharmaceutical", "pharmaceutical composition" or pharmaceutical formulation" encompasses "neutraceutical" also referred to as "nutraceutical"), "neutraceutical composition" or "neutraceutical formulation", respectively. Neutraceutical formulations or neutraceutical compositions may include a pharmaceutically acceptable carrier, such as those described herein.

The term "neutraceutical" or "nutraceutical" is a combination of the terms "nutritional" and "pharmaceutical". It refers to a composition, which is known or suspected in the art to positively affect human nutrition and/or health.

The term "beverage" describes any water-based liquid, which is suitable for human consumption (i.e., food-grade). A typical beverage of the present application is any "original beverage" in combination with at least one bioactive lipophilic molecule of the present application. "Original beverage" can be any beverage (e.g., any marketed beverage). The term "original beverage" includes beers, carbonated and non-carbonated waters (e.g., table waters and mineral waters), flavored waters (e.g., fruit-flavored waters), mineralized waters, sports drinks (e.g., Gatorade®), smoothies, neutraceutical drinks, filtered or non-filtered fruit and vegetable juices (e.g., apple juice, orange juice, cranberry juice, pineapple juice, lemonades and combinations thereof) including those juices prepared from concentrates. Exemplary juices include fruit juices having 100% fruit juice (squeezed or made from concentrate), fruit drinks (e.g., 0-29% juice), nectars (e.g., 30-99% juice). The term "original beverage" also includes fruit flavored beverages, carbonated drinks, such as soft-drinks, fruit-flavored carbonates and mixers. Soft drinks include caffeinated soft drinks, such as coke (e.g., Pepsi Cola®, Coca Cola®) and any "diet" versions thereof (e.g., including non-sugar sweeteners). The term "original beverage" also includes teas (e.g., green and black teas, herbal teas) including instant teas, coffee, including instant coffee, chocolate-based drinks, malt-based drinks, milk, drinkable dairy products and beer. The term "original beverage" also includes any liquid or powdered concentrates used to make beverages.

The term "clear beverage" (e.g., clear juice) means any beverage clear (e.g., transparent) to the human eye. Typical clear beverages include carbonated or non-carbonated waters, soft drinks, such as Sprite®, Coke® or root beer, filtered juices and filtered beers. Typical non-clear beverages include orange juice with pulp and milk.

The term "non-alcoholic beverage" includes beverages containing essentially no alcohol. Exemplary non-alcoholic beverages include those listed above for the term "beverage". The term "non-alcoholic beverage" includes beers, including those generally referred to as "non-alcoholic beers". In one example, the non-alcoholic beverage includes less than about 10% alcohol by volume. In another example, the non-alcoholic beverage includes less than about 9% or less than about 8% alcohol by volume. In yet another example, the non-alcoholic beverage includes less than about 7%, less than about 6% or less than about 5% alcohol by volume.

The term "essentially stable to chemical degradation" refers to a bioactive molecule of the present application as contained in a formulation (e.g., aqueous formulation), beverage or other composition of the present application. In one example, "essentially stable to chemical degradation" means that the molecule is stable in its original (e.g., reduced) form and is not converted to another species (e.g., oxidized species; any other species including more or less atoms; any other species having an essentially different molecular structure), for example, through oxidation, cleavage, rearrangement, polymerization and the like, including those processes induced by light (e.g., radical mechanisms). Examples of chemical degradation include oxidation and/or cleavage of double bonds in unsaturated fatty acids and light-induced rearrangements of unsaturated molecules. Certain degradation products of omega-3-fatty acids include aldehydes. The molecule is considered to be essentially stable when the concentration of its original (e.g., reduced) form in the composition (e.g., aqueous formulation) is not significantly diminished over time. For example, the molecule is essentially stable when the concentration of the original form of the molecule remains at least 80% when compared with the concentration of the original form of the molecule at about the time when the composition was prepared. In another example, the molecule is essentially stable when the concentration of the original form remains at least about 85%, at least about 90% or at least about 95% of the original concentration. For example, an aqueous composition containing omega-3-fatty acids at a concentration of about 50 mg/ml is considered essentially stable for at least 90 days when, at the end of the 90 days, the concentration of omega-3-fatty acids in the aqueous composition remains at least about 40 mg/ml (80% of 50 mg/ml).

The term "essentially clear" is used herein to describe the compositions (e.g., formulations) of the present application. For example, the term "essentially clear" is used to describe an aqueous formulation or a beverage of the present application. In one example, clarity is assessed by the normal human eye. In this example, "essentially clear" means that the composition is transparent and essentially free of visible particles and/or precipitation (e.g., not visibly cloudy, hazy or otherwise non-homogeneous). In another example, clarity, haziness or cloudiness of a composition is assessed using light scattering technology, such as dynamic light scattering (DLS), which is useful to measure the sizes of particles, e.g., micelles, contained in a composition. In one example, "essentially clear" means that the median particle size as measured by DLS is less than about 100 nm. For example, when the median particle size is less than 100 nm the liquid appears clear to the human eye. In another example, "essentially clear" means that the median particle size is less than about 80 nm. In yet another example, "essentially clear" means that the median particle size is less than about 60 nm. In a further example, "essentially clear" means that the median particle size is less than about 40 nm. In another example, "essentially clear" means that the median particle size is between about 20 and about 30 nm. A person of skill in the art will know how to prepare a sample for DLS measurement. For example, in order to prepare a sample (e.g., formulation of the present application) for a DLS measurement, the sample is typically diluted so that the concentration of the solubilizing agent in the diluted sample is between about 1 mM ($10^{-3}$ M) and 0.01 mM ($10^{-5}$ M). In another example, the solubilizing agent (e.g., TWEEN-85, TPGS or TPGS-1000) is present in a concentration that is above the critical micelle concentration (CMC) (i.e., the concentration that allows for spontaneous formation of micelles in water). For example, a typical CMC for TPGS in water is about 0.1 to about 0.5 mg/ml. A person of skill in the art will be able to select suitable concentrations in order to successfully measure particle sizes in a formulation of the present application.

Alternatively, clarity, haziness or cloudiness of a composition of the present application can be determined by measuring the turbidity of the sample. This is especially useful when the composition is a beverage (e.g., water, soft-drink etc.). In one example, turbidity is measured in FTU (Formazin Turbidity Units) or FNU (Formazin Nephelometric Units). In one example, turbidity is measured using a nephelometer. Nephelometric measurements are based on the light-scattering properties of particles. The units of turbidity from a calibrated nephelometer are called Nephelometric Turbidity Units (NTU). In one example, reference standards with known turbidity are used to measure the turbidity of a sample. In one example, a composition of the present application (e.g., a beverage of the present application) is "essentially clear" when the turbidity is not more than about 500% higher than the control (original beverage without an added lipophilic bioactive molecule of the present application, but optionally including a solubilizing agent of the present application). For example, the turbidity of a sample of flavored water is measured to be 2.0 ntu and the turbidity of another sample containing the same flavored water in combination with a fatty acids is measured to be at or below about 8.0 ntu (2.0 ntu+300%=8.0 ntu), then the fatty acids sample is considered to be essentially clear. In another example, a composition of the present application is "essentially clear" when the turbidity is not more than about 300% higher than the control. In yet another example, a composition of the present application is "essentially clear" when the turbidity is not more than about 200%, about 150% or about 100% higher than the control. In a further example, a composition of the present application is "essentially clear" when the turbidity is not more than about 80%, about 60%, about 40%, about 20% or about 10% higher than the control.

The term "emulsion" as used herein refers to a lipophilic molecule of the present application emulsified (solubilized) in an aqueous medium using a solubilizing agent of the present application. In one example, the emulsion includes micelles formed between the lipophilic molecule(s) and the solubilizing agent. When those micelles are sufficiently small, the emulsion is essentially clear. Typically, the emulsion will appear clear (e.g., transparent) to the normal human eye, when those micelles have a median particle size of less than 100 nm. In one example, the micelles in the emulsions of the present application have median particle sizes below 60 nm. In a typical example, micelles formed in an emulsion of the present application have a median particle size between about 20 and about 30 nm. In another example, the emulsion is stable, which means that separation between the aqueous phase and the lipophilic component does essentially not occur (e.g., the emulsion stays clear). A typical aqueous medium, which is used in the emulsions of the present application, is water, which may optionally contain other solubilized molecules, such as salts, coloring agents, flavoring agents and the like. In one example, the aqueous medium of the emulsion does not include an alcoholic solvent, such as ethanol or methanol.

The term "micelle" is used herein according to its art-recognized meaning and includes all forms of micelles, including, for example, spherical micelles, cylindrical micelles, worm-like micelles and sheet-like micelles, and vesicles, formed in water, or mostly water.

The term "flavonoid" as used herein is recognized in the art. The term "flavonoid" includes those plant pigments found in many foods that are thought to help protect the body from disease (e.g., cancer). These include, for example, epi-gallo catechin gallate (EGCG), epi-gallo catechin (EGC) and epi-catechin (EC).

The term "tocopherol" includes all tocopherols, including alpha-, beta-, gamma- and delta tocopherol. The term "tocopherol" also includes tocotrienols.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "alkyl," by itself or as part of another substituent, means, unless otherwise stated, a straight or branched chain, or cyclic hydrocarbon radical, or combination thereof, which can be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl" with the difference that the heteroalkyl group, in order to qualify as an alkyl group, is linked to the remainder of the molecule through a carbon atom. Alkyl groups that are limited to hydrocarbon groups are termed "homoalkyl".

The term "alkenyl" by itself or as part of another substituent is used in its conventional sense, and refers to a radical derived from an alkene, as exemplified, but not limited, by substituted or unsubstituted vinyl and substituted or unsubstituted propenyl. Typically, an alkenyl group will have from 1 to 24 carbon atoms. In one aspect, the alkenyl groups have from 1 to 10 carbon atoms.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms. In one aspect, the groups may have 10 or fewer carbon atoms. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, S, B and P and wherein the nitrogen and sulfur atoms can optionally be oxidized and the nitrogen heteroatom can optionally be quaternized. The heteroatom(s) can be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms can be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2R'$— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. A "cycloalkyl" or "heterocycloalkyl" substituent can be attached to the remainder of the molecule directly or through a linker. An exemplary linker is alkylene. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, 1-piperazinyl, 2-piperazinyl, and the like.

The terms "halo" or "halogen," by themselves or as part of another substituent, mean, unless otherwise stated, a fluorine, chlorine, bromine or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (e.g., from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

The term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen.

Each of the above terms (e.g., "alkyl," "heteroalkyl," "aryl" and "heteroaryl") are meant to include both substituted and unsubstituted forms of the indicated radical.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', 'N—OR', —NR'R", —SR', -halogen, —SiR'R"R'", —OC(O)R', —C(O)R', —$CO_2R'$, —CONR'R", —OC(O)NR'R", —NR"C(O)R', —NR'—C(O)NR"R'", —NR"C(O)$_2R'$, —NR—C(NR'R"R'")=NR"", —NR—C(NR'R")=NR'", —S(O)R', —S(O)$_2R'$, —S(O)$_2$NR'R", —$NRSO_2R'$, —CN and —$NO_2$ in a number ranging from zero to (2 m'+1), where m' is the total number of carbon atoms in such radical. R', R", R'" and R"" each independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the present application includes more than one R group, for example, each of the R groups is independently selected as are each R', R", R'" and R"" groups when more than one of these groups is present. Substituents on an aryl or heteroaryl groups are as provided for substituents on an alkyl group as defined above.

The term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

The term "fused ring system" means at least two rings, wherein each ring has at least 2 atoms in common with another ring. "Fused ring systems can include aromatic as well as non aromatic rings. Examples of "fused ring systems" are naphthalenes, indoles, quinolines, chromenes and the like.

The term "heteroatom" includes oxygen (O), nitrogen (N), sulfur (S), silicon (Si) and boron (B).

The symbol "R" is a general abbreviation that represents a substituent group. Exemplary substituent groups include substituted or unsubstituted alkyl, substituted or unsubstituted heteroalkyl, substituted or unsubstituted aryl, substituted or unsubstituted heteroaryl, and substituted or unsubstituted heterocycloalkyl groups.

The term "metal chelator" or "metal chelating moiety" as used herein refers to a compound that combines with a metal ion, such as iron, to form a chelate structure. The chelating agents form coordinate covalent bonds with a metal ion to form the chelates. Accordingly, chelates are coordination compounds in which a central metal atom is bonded to two or more other atoms in at least one other molecule (ligand) such that at least one heterocyclic ring is formed with the metal atom as part of each ring. For the purposes of the present application, the metal chelator has demonstrated affinity for iron. These ions may be free in solution or they may be sequestered by a metal ion-binding moiety. The term "metal ion" as used herein refers to any physiological, environmental and/or nutritionally relevant metal ion. Such metal ions include certain metal ions such as iron, but may also include lead, mercury and nickel. When EDTA (or disodium EDTA or calcium disodium EDTA) is used in the present application to chelate iron, the chelate forms a $Fe^{3+}$ ethylene-diaminetetraacetic acid (EDTA) complex.

The term "pharmaceutically acceptable salts" includes salts of the active compounds which are prepared with relatively nontoxic acids or bases, depending on the particular substituents found on the compounds described herein. When compounds of the present application contain relatively acidic functionalities, base addition salts can be obtained by contacting the neutral form of such compounds with a sufficient amount of the desired base, either neat or in a suitable inert solvent. When compounds of the present application contain relatively basic functionalities, acid addition salts can be obtained by contacting the neutral form of such compounds with a sufficient amount of the desired acid. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., Journal of Pharmaceutical Science, 66: 1-19 (1977)). Certain specific compounds of the present application contain both basic and acidic functionalities that allow the compounds to be converted into either base or acid addition salts.

When a residue is defined as "O−", then the formula is meant to optionally include an organic or inorganic cationic counterion. For example, the resulting salt form of the compound is pharmaceutically acceptable.

The neutral forms of the compounds are, for example, regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present application.

Certain compounds of the present application possess asymmetric carbon atoms (chiral centers) or double bonds; the racemates, diastereomers, geometric isomers and individual isomers are encompassed within the scope of the present application. The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the present application can exist in particular geometric or stereoisomeric forms. The present application contemplates all such compounds, including cis- and trans-isomers, (−)- and (+)-enantiomers, diastereomers, (D)-isomers, (L)-isomers, the racemic mixtures thereof. All such isomers, as well as mixtures thereof, are intended to be included in this present application.

"Ring" as used herein means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 to 7 atoms in the encircling arrangement. The ring optionally includes a heteroatom. Thus, the term "5- to 7-membered ring" includes, for example pyridinyl and piperidinyl. The term "ring" further includes a ring system comprising more than one "ring", wherein each "ring" is independently defined as above.

"Substituted or unsubstituted" or "optionally substituted" means that a group such as, for example, alkyl, aryl, heterocyclyl, $(C_1-C_8)$cycloalkyl, heterocyclyl$(C_1-C_8)$alkyl, aryl $(C_1-C_8)$alkyl, heteroaryl, heteroaryl$(C_1-C_8)$alkyl, and the like, unless specifically noted otherwise, may be unsubstituted or, may substituted by 1, 2 or 3 substituents selected from the group such as halo, nitro, trifluoromethyl, trifluoromethoxy, methoxy, carboxy, —$NH_2$, —OH, —SH, —$NHCH_3$, —$N(CH_3)_2$, —SMe, cyano and the like.

In one embodiment, there is provided aqueous compositions including a lipophilic bioactive molecule and a solubilizing agent described herein. In a particular aspect, the lipophilic bioactive molecule is omega-fatty acids (e.g., omega-3-, omega-6- or omega-9-fatty acids). In another embodiment, the omega-fatty acids are the non-natural omega-fatty acids that are the omega-3-, omega-6- and omega-9-fatty acids ethyl esters. In yet another embodiment, the omega-fatty acids is the $C_1$-$C_{10}$ alkyl esters, the $C_1$-$C_5$ alkyl esters, the $C_1$-$C_3$ alkyl esters or the $C_2$-$C_5$ alkyl esters. In yet another embodiment, the omega-fatty acids is a mixture of the natural and the non-natural omega-fatty acids.

In one embodiment, the weight to weight (w/w) ratio of the natural omega-fatty acids to the non-natural omega-fatty acids used in the compositions of the present application is about 100:1, about 95:5, about 90:10, about 80:20, about 70:30, about 60:40, about 55:45, about 50:50, about 45:55, about 40:60, about 30:70, about 20:80, about 10:90, about 5:95 or about 1:100.

In another embodiment, the formulation comprises substantially pure omega-fatty acids ethyl esters that are free from omega-fatty acids glycerides, or that contains no omega-fatty acids glycerides. In another embodiment, the formulation comprises the omega-fatty acids esters, such as the ethyl esters, that is greater than 35% pure, greater than 45% pure, greater than 55% pure, greater than 65% pure, greater than 75% pure, greater than 85% pure, greater than 90% pure or greater than 95% pure. In another embodiment, the omega-fatty acid ethyl esters is greater than 98% pure. In another embodiment of the above, the formulation comprises substantially pure EPA and DHA esters, such as substantially pure EPA/DHA ethyl esters. In another aspect, the omega-3 may be enriched with DHA esters, or enriched with EPA esters. In another aspect, the omega-3 has an DHA:EPA ratio of about 1:1, 1:2, 1:3 or 1:5.

In one embodiment, the composition comprising the lipophilic bioactive molecules of the present application further comprises a mixture of omega-fatty acids and at least a second lipophilic bioactive molecule. In one aspect, the second lipophilic bioactive molecule is ubiquinone (e.g., $CoQ_{10}$). In another embodiment, the weight to weight (w/w) ratio of the ubiquinone to the natural omega-fatty acids or the weight to weight (w/w) ratio of the ubiquinone to the non-natural omega-fatty acids, used in the compositions of the present application is about 100:1, about 95:5, about 90:10, about 80:20, about 70:30, about 60:40, about 55:45, about 50:50, about 45:55, about 40:60, about 30:70, about 20:80, about 10:90, about 5:95 or about 1:100. In one embodiment of the above, the omega-fatty acid is the omega-fatty acid ethyl esters, such as the $C_1$-$C_{10}$ alkyl esters, the $C_1$-$C_5$ alkyl esters, the $C_1$-$C_3$ alkyl esters or the $C_2$-$C_5$ alkyl esters. In a particular variation of the above, the omega-fatty acid ester is the ethyl ester. In another embodiment of the formulation, the lipophilic bioactive molecule is the natural omega-fatty acid in combination with the non-natural omega-fatty acid combined with a different lipophilic molecule, as provided herein. In another embodiment, the lipophilic bioactive molecule is the natural omega-fatty acid or the non-natural omega-fatty acid combined with a different lipophilic molecule.

These formulations have several advantages. First, they provide a lipophilic bioactive molecule (e.g., a bioactive molecule that is normally essentially water-insoluble) in an essentially clear, aqueous solution. This formulation can enable a consumer to ingest the lipophilic bioactive molecule in a liquid form, for example, in a beverage, such as water. The aqueous formulations are essentially clear, which makes the formulations more appealing to a consumer. In another embodiment, the present application provides formulations (e.g., aqueous formulations) of lipophilic bioactive molecules (e.g., natural and non-natural omega-fatty acids including omega-3-, omega-6- or omega-9-fatty acids, and their esters, as defined herein) that include a solubilizing agent described herein, as well as a water-soluble reducing agent (also referred to as a stabilizer). The lipophilic bioactive molecules in these formulations (especially aqueous formulations) are stable with respect to chemical degradation (e.g., oxidation). In one example, the chemical stability of the lipophilic compounds is a result of a synergistic effect between the nature of the solubilizing agent and the water-solubility of the reducing agent (stabilizer): The solubilizing agent is an amphiphilic, nonionic surfactant, which in aqueous solutions allows the lipophilic molecule to be emulsified in "nanomicelles", which typically have an average particle size of not more than 150 nm, often below 30 nm. When the lipophilic molecule is solubilized in the form of these small micelles, a water-soluble (as opposed to lipid-soluble) reducing agent is surprisingly effective in preventing chemical degradation of the lipophilic molecule in an aqueous solution. For example, the addition of a water-soluble reducing agent diminishes or prevents the degradation of the lipophilic bioactive molecule and extends its average lifetime in solution, for example by at least 5 times. Molecules that are vulnerable to oxidation in aqueous solutions include omega-fatty acids (e.g., omega-3-, omega-6- or omega-9-fatty acids; or DHA).

In another example, the water-soluble reducing agent itself can be a compound with potential health benefits (e.g., vitamin C and other vitamins). The combination of two beneficial ingredients (lipophilic bioactive molecule and stabilizer) in a single composition provides greater convenience to a consumer. Another benefit is that the surfactant supplies a nutrient in water (e.g., vitamin E, CoQ10, etc.).

The present application also provides a method for making aqueous, water-soluble omega-fatty acids (e.g., omega-3-, omega-6- or omega-9-fatty acids) formulation of the present application. An exemplary process includes contacting an emulsion of omega-3-fatty acids in an aqueous medium (e.g., water) with a water-soluble reducing agent (e.g., vitamin C or a water-soluble derivative of vitamin C) and a metal chelating agent, such as ethylenediamine tetraacetic acid (EDTA). In addition, the process includes contacting the omega-3-fatty acids in an aqueous medium with a water-soluble reducing agent, a metal chelating agent, and an aldehyde sequestering (by direct addition), or reducing agent, such as sodium bisulfite.

In one example, the omega-fatty acids emulsion is formed using a solubilizing agent of the present application. In one example, the aqueous omega-3-fatty acids formulation thus formed is substantially clear. The water-soluble formulations of the present application may be used to prepare beverages having omega-fatty acids dissolved therein.

Compositions:

The present application provides formulations of lipophilic bioactive molecules. In one embodiment, the lipophilic bioactive molecule is omega-fatty acids (e.g., the natural and non-natural omega-fatty acids including omega-3-, omega-6- or omega-9-fatty acids, and their esters, as defined herein). In another embodiment, the lipophilic bioactive molecule is a non-natural omega-fatty acids that are the omega-3-, omega-6- and omega-9-fatty acids ethyl esters. In yet another embodiment, the lipophilic bioactive molecule is the omega-fatty acid that is the $C_1$-$C_{10}$ alkyl esters, the $C_1$-$C_5$ alkyl esters, the $C_1$-$C_3$ alkyl esters or the $C_2$-$C_5$ alkyl esters. In yet another embodiment, the lipophilic bioactive molecule is an omega-fatty acids that is a mixture of the natural and the non-natural omega-fatty acids. In one embodiment, the oil comprising the omega-fatty acids has a high concentration of the ester, such as the omega-fatty acid ethyl esters. In one aspect, the concentration of the ethyl esters is at least about 60% of the oil. In another aspect, the concentration of the ethyl esters is at least about 70% of the oil. In another aspect, the concentration of the ethyl esters is at least about 80% of the oil. In another aspect, the concentration of the ethyl esters is at least about 90% of the oil. In another aspect, the concentration of the ethyl esters is at least about 95% of the oil.

In yet another embodiment, the lipophilic bioactive molecule as provided herein further comprises a mixture of omega-fatty acids and at least a second lipophilic bioactive molecule. In one aspect, the second lipophilic bioactive molecule is ubiquinone (e.g., $CoQ_{10}$).

In one embodiment, the formulations comprise at least (a) a lipophilic bioactive molecule or mixtures of bioactive molecules, as disclosed above, (b) a solubilizing agent, and (c) a metal chelating agent. In another embodiment, the formulations comprise at least (a) a lipophilic bioactive molecule or mixtures of bioactive molecules, as disclosed above, (b) a solubilizing agent, (c) a water-soluble reducing agent, (d) a metal chelating agent, and e) an agent reactive towards aldehydes, such as sodium bisulfite. In one embodiment, the formulations comprise at least (a) an omega-fatty acids of the present application, (b) a solubilizing agent, and (c) a metal chelating agent. In another embodiment, the formulations comprise at least (a) an omega-fatty acids of the present application, (b) a solubilizing agent, (c) a water-soluble reducing agent, (d) a metal chelating agent, and (e) an agent reactive towards aldehydes, such as sodium bisulfite. The inventors have discovered that certain lipophilic bioactive molecules, such as omega-3-fatty acids in particular, which are normally prone to chemical degradation (e.g., oxidation) can be stabilized using a combination of stabilizing agents that work both inside the micelar array, and outside in the aqueous medium. Thus, this approach includes a water-soluble reducing agent, when the molecule is formulated using a solubilizing agent of the present application (any micelle-forming surfactant; e.g., TPGS). An exemplary water-soluble reducing agent is selected from ascorbic acid (vitamin C) and water-soluble derivatives of vitamin C. Vitamin C is a convenient reducing agent because it is widely available and suitable for human consumption. In addition, aldehydes that are generated as by-products of degradation and result in undesirable smell and/or taste, may be neutralized by the addition of a reagent that reacts with the aldehyde, such as a bisulfite.

It was determined that water-soluble species that react with aldehydic by-products of oxidation (e.g., bisulfite, forming bisulfite addition compounds) are very effective in tandem with lipid-soluble reducing agents with respect to their capabilities to chemically stabilize lipophilic molecules in aqueous solutions. The present application further provides methods of making the formulations. The formulations of the present application can be used in a variety of products, such as foods, beverages, cosmetics and skin-care products (topical application), dietary supplements (e.g., formulated in soft-gelatine capsules) and nutraceuticals. In one embodiment, the present application provides a beverage including a formulation of the present application.

The following abbreviations are used throughout the application: Ub50-omega-3-fatty acid-50; TPGS—polyoxyethanyl-a-tocopheryl succinate (e.g., TPGS-1000, TPGS-600). A number following one of the above abbreviations (e.g., TPGS-600) indicates an average molecular weight of the polyoxyethanyl or poly(ethylene glycol) (PEG) moiety of the compound. A number followed by the abbreviation "Me" (e.g., TPGS-1000Me) indicates a polyoxyethanyl moiety capped with a methyl group (methoxypolyoxyethanyl or mPEG).

Formulations:

In one embodiment, the present application provides a water-soluble formulation including a bioactive agent or mixtures of bioactive agents as disclosed herein (e.g., a combination of omega-3s, and CoQ10 or ubiquinol), one or more water-soluble reducing agents, and a solubilizing agent of the present application. An alternative embodiment includes the above ingredients, but may rely on more than one solubilizing agent within any given formulation; i.e., a combination of surfactants (e.g., TPGS, TPGS-1000 or TWEEN-85, in any ratio). In one aspect, the present application provides a water-soluble formulation including natural omega-fatty acids or non-natural omega-fatty acids (e.g., omega-3-, omega-6- or omega-9-fatty acids and their esters, as defined herein), a water-soluble reducing agent and a solubilizing agent of the present application. In one example, the solubilizing agent has a structure according to Formula (I):

    (I)

wherein:
a is 0 and 1;
$L^1$ is a linker moiety that covalently links the hydrophobic moiety Z and the hydrophilic moiety $Y^1$;
$Y^1$ is a linear or branched hydrophilic linker moiety comprising at least one polymeric moiety independently selected from poly(alkylene oxides) (e.g., PEG) and polyalcohols, and monoethers; and
Z is a hydrophobic moiety.

In another embodiment, there is provided a method for stabilizing a substantially water insoluble lipophilic bioactive compound selected from the group consisting of omega-3 fatty acid, omega-6 fatty acid, omega-9 fatty acid, omega-12 fatty acid, and the non-glyceride esters of the omega-fatty acids, and mixtures thereof, in an aqueous solution comprising contacting the lipophilic bioactive compound, with a composition comprising a micelle-forming surfactant for a sufficient period of time to dissolve the lipophilic bioactive compound.

In another embodiment, there is provided a stabilized aqueous formulation comprising a substantially water insoluble lipophilic bioactive compound selected from the group consisting of omega-3 fatty acid, omega-6 fatty acid, omega-9 fatty acid, omega-12 fatty acid and combinations thereof, and a micelle-forming surfactant selected from the group consisting TPGS (polyoxyethanyl-a-tocopheryl succinate) and combinations thereof, wherein the formulation remains substantially stable when stored at or below room temperature for a period of at least 6 months or at least 12 months.

In another embodiment, there is provided a stable, water soluble formulation comprising:
a) an omega-fatty acids;
b) one or more solubilizing agent selected from the group consisting of solubilizing agents having a hydrophilic-lipophilic balance (HLB) of 8-18, HLB of 7-9 and HLB of 8-12, HLB of 13-15, or mixtures thereof; and
c) one or more additives selected from the group consisting of a metal chelator, a water soluble reducing agent, a water-insoluble reducing agent, a bisulfite salt, a metabisulfite salt or mixtures thereof.

In one embodiment, the above stable soluble formulation is an oxidatively stable formulation. That is, the formulation comprising omega-3 ethyl ester remains stable toward oxidation or is resistant toward oxidation for a commercially useful period of time, depending on the formulation and the commercial use for the formulation. In another embodiment, the stable soluble formulation is stable and does not oil out, or where desired, does not form cloudy solutions.

In one aspect of the above embodiment, the solubilizing agent comprises the Formula (I):

    (I)

wherein:
a is 0 and 1;
$L^1$ is a linker moiety that covalently links the hydrophobic moiety Z and the hydrophilic moiety $Y^1$;
$Y^1$ is a linear or branched hydrophilic moiety comprising at least one polymeric moiety independently selected from poly(alkylene oxides) and polyalcohols; and
Z is a hydrophobic moiety.

In one aspect of the formulation, the solubilizing agent is selected from the group consisting of TPGS (polyoxyethanyl-a-tocopheryl succinate), TPGS-1000 (D-alpha-tocopheryl polyethylene glycol 1000 succinate) and combinations thereof.

In another aspect of the above, the omega-fatty acid is selected from the group consisting of omega-3 fatty acid, omega-6 fatty acid, omega-9 fatty acid, omega-12 fatty acid, the glyceride esters of the omega-fatty acids, and the non-glyceride esters of the omega-fatty acids, and mixtures thereof. In one variation of the omega-fatty acids, the omega-fatty acids is the ethyl esters or the glyceride esters. In another aspect of the above, the omega-fatty acids is selected from the group consisting of α-linolenic acid (ALA), stearidonic acid, eicosatetraenoic acid, eicosapentaenoic acid (EPA), docosapentaenoic acid, docosahexaenoic acid (DHA), linoleic acid, gamma-linolenic acid, eicosadienoic acid, dihomo-gamma-linolenic acid, arachidonic acid, docosadienoic acid, adrenic acid, docosapentaenoic acid, oleic acid, eicosenoic acid, mead acid, erucic acid and nervonic acid, and combinations thereof. In another aspect of the above, the solubilizing agent comprises the Formula (I), wherein:

Z is selected from the group consisting of sterols, tocopherols, tocotrienol and omega-fatty acids and derivatives or homologues thereof;

$L^1$ is selected from a single bond, substituted or unsubstituted alkylene, substituted or unsubstituted heteroalkylene, substituted or unsubstituted arylene, substituted or unsubstituted heteroarylene and substituted or unsubstituted heterocycloalkylene; and $Y^1$ is a linear or branched hydrophilic moiety including at least one polymeric moiety, wherein each polymeric moiety is a member independently selected from poly(alkylene oxides) and polyalcohols.

In another aspect of the above formula:

$Y^1$ is selected from the group consisting of poly(alkylene oxides) and monoethers therefrom, polyalcohols, polysaccharides, polyamino acids, polyphosphoric acids, polyamines and derivatives thereof; and $L^1$ is selected from the group consisting of a linear or branched $C_2, C_3, C_4, C_5, C_6, C_7, C_8, C_9, C_{10}, C_{11}, C_{12}, C_{13}, C_{14}, C_{15}, C_{16}, C_{17}, C_{18}, C_{19}, C_{20}, C_{21}, C_{22}, C_{23}, C_{24}$ or $C_{25}$-$C_{30}$ alkylene chain, optionally incorporating at least one functional group selected from the group consisting of ether, thioether, ester, carboxamide, sulfonamide, carbonate and urea groups.

In another aspect of the water soluble formulation, the solubilizing agent is TPGS (polyoxyethanyl-a-tocopheryl succinate) or TPGS-1000 (D-alpha-tocopheryl polyethylene glycol 1000 succinate), wherein the tocopheryl is the natural tocopherol isomer or the un-natural tocopherol isomer. In yet another aspect, the solubilizing agent is selected from the group consisting of Poloxamer 188, Polysorbate 80, Polysorbate 20, Vit E-TPGS, Solutol HS 15, PEG-40 Hydrogenated castor oil (Cremophor RH40), PEG-35 Castor oil (Cremophor EL), PEG-8-glyceryl capylate/caprate (Labrasol), PEG-32-glyceryl laurate (Gelucire 44/14), PEG-32-glyceryl palmitostearate (Gelucire 50/13); Polysorbate 85, Polyglyceryl-6-dioleate (Caprol MPGO), Mixtures of high and low HLB emulsifiers; Sorbitan monooleate (Span 80), Capmul MCM, Maisine 35-1, Glyceryl monooleate, Glyceryl monolinoleate, PEG-6-glyceryl oleate (Labrafil M 1944 CS), PEG-6-glyceryl linoleate (Labrafil M 2125 CS), Oleic acid, Linoleic acid, Propylene glycol monocaprylate (e.g. Capmul PG-8 or Capryol 90), Propylene glycol monolaurate (e.g., Capmul PG-12 or Lauroglycol 90), Polyglyceryl-3 dioleate (Plurol Oleique CC497), Polyglyceryl-3 diisostearate (Plurol Diisostearique) and Lecithin with and without bile salts, or combinations thereof. In another aspect, the water-soluble or water-insoluble reducing agent is selected from the group consisting of L-ascorbic acid-6-palmitate, vitamin C and its salts, alpha, beta, gamma and delta tocopherol or mixtures of tocopherol and alpha, beta, gamma, and delta-tocotrienols or mixtures thereof.

In one aspect of the above formulation, the metal chelator is selected from the group consisting of ethylenediaminetetraacetic acid (EDTA), disodium EDTA and calcium disodium EDTA and mixtures thereof. In another aspect, the bisulfite is sodium bisulfite, potassium bisulfite, sodium metabisulfite or potassium metabisulfite. In another aspect of the formulation, when dissolved in water, provides a solution with a clarity range of about 1,000 to 20 NTU, about 100 to 20 NTU, about 55 to 35 NTU or about 20 to 35 NTU. In another aspect of the formulation, when dissolved in water, provides a solution that remains stable toward degradation when stored at or below room temperature for a period of at least 6 months or at least 12 months. In one aspect of the present method, the lipophilic bioactive compound is selected from the group consisting of a natural omega-fatty acids, a non-natural omega-fatty acids, a non-naturally omega-fatty acids ethyl esters, a non-naturally omega-fatty acids esters that is the $C_1$-$C_{10}$ alkyl esters, the $C_1$-$C_5$ alkyl esters, the $C_1$-$C_3$ alkyl esters or the $C_2$-$C_5$ alkyl esters, and mixtures thereof. In another aspect of the above, the solubilizing agent to omega-3 fatty acids is less than or equal to 2:1 to 0.5 to 1.

In another embodiment, there is provided a method for stabilizing a substantially water insoluble lipophilic bioactive compound selected from the group consisting of omega-3 fatty acid, omega-6 fatty acid, omega-9 fatty acid, omega-12 fatty acid, the glyceride esters and non-glyceride esters of the omega-fatty acids, and mixtures thereof, in an aqueous solution, the method comprising contacting the lipophilic bioactive compound with:

a) a composition comprising one or more solubilizing agents selected from the group consisting of solubilizing agents having a hydrophilic-lipophilic balance (HLB) of 8-18, HLB of 7-9 and HLB of 8-12, HLB of 13-15, or mixtures thereof; and c) one or more additives selected from the group consisting of a metal chelator, a water soluble reducing agent, a water-insoluble reducing agent, a bisulfite salt, a metabisulfite salt or mixtures thereof, for a sufficient period of time to dissolve the lipophilic bioactive compound. In one aspect of the above, the solubilizing agent comprises the Formula (I):

$$Y^1\text{-}[L^1]_a\text{-}Z \qquad (I)$$

wherein:

a is 0 and 1;

$L^1$ is a linker moiety that covalently links the hydrophobic moiety Z and the hydrophilic moiety $Y^1$;

$Y^1$ is a linear or branched hydrophilic moiety comprising at least one polymeric moiety independently selected from poly(alkylene oxides) and polyalcohols; and is a hydrophobic moiety. In another aspect, the solubilizing agent is selected from the group consisting of TPGS (polyoxyethanyl-a-tocopheryl succinate), TPGS-1000 (D-alpha-tocopheryl polyethylene glycol 1000 succinate) and combinations thereof. In yet another aspect, the dissolved aqueous composition provides a semi-cloudy or substantially clear solution with a clarity range of about 1,000 to 20 NTU, about 100 to 20 NTU, about 35 to 55 NTU or about 20 to 35 NTU. In one aspect of the above, the method provides contacting the lipophilic bioactive compound with the composition comprising the solubilizing agent for a sufficient period of time to dissolve the lipophilic bioactive compound is performed at an elevated temperature. In another aspect, of the method, the metal chelator is ethylenediaminetetraacetic acid (EDTA), disodium EDTA and calcium disodium EDTA or mixtures thereof.

In another embodiment, there is provided a stabilized aqueous emulsion of omega-3 fatty acid comprising:

a) omega-3 fatty acid;

b) one or more solubilizing agents selected from the group consisting of solubilizing agents having a hydrophilic-lipophilic balance (HLB) of 8-18, HLB of 7-9 and HLB of 8-12, HLB of 13-15, or mixtures thereof; and c) one or more additives selected from the group consisting of a metal chelator, a water soluble reducing agent, a water-insoluble reducing agent, a bisulfite salt, a metabisulfite salt or mixtures thereof;

d) a carrier or additive selected from the group consisting of HI-CAP 100 (National Starch), Emcap Starch, TICAMULSION FC (TIC GUMS), Spray gum F (gum acacia with Maltrin-100), natural vanillin, natural maltol, maltodextrin 10-DE and mixtures thereof;
e) calcium disodium EDTA or disodium EDTA;
f) sodium bisulfite, sodium metabisulfite, potassium bisulfite or potassium metabisulfite; and
g) water, wherein the emulsion remains stable toward degradation when stored at or below room temperature for a period of at least 6 months or at least 12 months.

In one aspect of the above, the solubilizing agent comprises the Formula (I):

$$Y^1-[L^1]_a-Z \qquad (I)$$

wherein:
a is 0 and 1;
$L^1$ is a linker moiety that covalently links the hydrophobic moiety Z and the hydrophilic moiety $Y^1$;
$Y^1$ is a linear or branched hydrophilic moiety comprising at least one polymeric moiety independently selected from poly(alkylene oxides) and polyalcohols; and
Z is a hydrophobic moiety. In another aspect of the above, the emulsion, when dissolved in water, provides a solution with a clarity range of about 1,000 to 20 NTU, about 100 to 20 NTU or about 20 to 35 NTU, and wherein the solution remains stable toward degradation when stored at or below room temperature for a period of at least 6 months or at least 12 months.

In another embodiment, there is provided a stabilized powder composition of omega-3 fatty comprising:
a) omega-3 fatty acid;
b) TPGS (polyoxyethanyl-a-tocopheryl succinate);
c) a carrier or additive selected from the group consisting of HI-CAP 100 (National Starch), Emcap Starch, TICAMULSION FC (TIC GUMS), Spray gum F (gum acacia with Maltrin-100), natural vanillin, natural maltol, maltodextrin 10-DE and mixtures thereof;
d) calcium disodium EDTA or disodium EDTA; and
e) sodium bisulfite, potassium bisulfite, sodium metabisulfite or potassium metabisulfite; wherein the powder, when dissolved in water, provides a solution with a clarity range of about 1,000 to 20 NTU, about 100 to 20 NTU or about 20 to 35 NTU, and wherein the solution remains stable toward degradation when stored at or below room temperature for a period of at least 6 months or at least 12 months. In one aspect of the above, there is provided a stabilized food, beverage, pharmaceutical or nutraceutical product comprising the stabilized powder composition of the above. In one aspect, the stabilized powder composition of the present application, wherein the solution, suited for human consumption is further treated for the inactivation of microbes by a process selected from the group consisting of pasteurization, aseptic packaging, membrane permeation, sonication or combinations thereof.

In another embodiment, there is provided a method for preparing a dry powder composition comprising a stabilized omega-3 fatty acid composition, the method comprising the steps of:
(1) preparing an aqueous solution comprising a carrier or additive selected from the group consisting of HI-CAP 100 (National Starch), Emcap Starch, TICAMULSION FC (TIC GUMS), Spray gum F (gum acacia with Maltrin-100), natural vanillin, natural maltol, maltodextrin 10-DE and mixtures thereof;
(2) combining the solution comprising the carrier or additive with a stabilized aqueous emulsion of omega-3 fatty acid comprising:
a) an omega-3 fatty acid;
b) one or more solubilizing agents selected from the group consisting of solubilizing agents having a hydrophilic-lipophilic balance (HLB) of 8-18, HLB of 7-9 and HLB of 8-12, HLB of 13-15, and a solubilizing agent comprising the Formula (I):

$$Y^1-[L^1]_a-Z \qquad (I)$$

wherein:
a is 0 and 1;
$L^1$ is a linker moiety that covalently links the hydrophobic moiety Z and the hydrophilic moiety $Y^1$;
$Y^1$ is a linear or branched hydrophilic moiety comprising at least one polymeric moiety independently selected from poly(alkylene oxides) and polyalcohols; and
Z is a hydrophobic moiety; or mixtures thereof, and
c) one or more additives selected from the group consisting of a metal chelator, a water soluble reducing agent, a water-insoluble reducing agent, a bisulfite salt, a metabisulfite salt or mixtures thereof to form the pre-drying emulsion; and
(3) drying the emulsion to form the dry powder composition comprising the stabilized omega-3 fatty acid composition; wherein the powder, when dissolved in water, provides a solution that remains stable toward degradation when stored at or below room temperature for a period of at least 6 months or at least 12 months. In one aspect of the above, the solubilizing agent is TPGS (polyoxyethanyl-a-tocopheryl succinate) or TPGS-1000 (D-alpha-tocopheryl polyethylene glycol 1000 succinate). In another aspect of the method, the drying step comprises of a spray drying of the emulsion to form the powder.

In one aspect, Z is selected from the group consisting of sterols (e.g., cholesterol or sitosterol), tocopherols (e.g., alpha-tocopherol), tocotrienol and omega-fatty acids and derivatives or homologues thereof. In another aspect, the hydrophilic moiety is poly(ethylene glycol) (PEG) or methylated PEG (mPEG). The PEG moiety of the present application includes PEG-600 to PEG-2000. In one example, $L^1$ is selected from a single bond, substituted or unsubstituted alkylene, substituted or unsubstituted heteroalkylene, substituted or unsubstituted arylene, substituted or unsubstituted heteroarylene and substituted or unsubstituted heterocycloalkylene. In one embodiment, $L^1$ includes a linear or branched $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$ or $C_{25}$-$C_{30}$ alkylene chain, optionally incorporating at least one functional group. Exemplary functional groups according to this embodiment include ether, thioether, ester, carboxamide, sulfonamide, carbonate and urea groups. In a particular example, the solubilizing agent is selected from polyoxyethanyl-a-tocopheryl succinate (TPGS), TPGS-1000 (D-alpha-tocopheryl polyethylene glycol 1000 succinate) and combinations thereof. In one embodiment, the solubilizing agent is polyoxyethanyl-a-tocopheryl succinate (TPGS).

In one aspect, $Y^1$ is a linear or branched hydrophilic moiety including at least one polymeric moiety, wherein each polymeric moiety is a member independently selected from poly(alkylene oxides) (e.g., PEG) and polyalcohols. Exemplary lipophilic moieties are described herein, each of which is useful in this embodiment. In one example, the lipophilic moiety is poly(ethylene glycol) (PEG) or methylated PEG (mPEG). In one embodiment, $Y^1$ is selected from poly(alkylene oxides) (i.e., polyethers), polyalcohols, polysaccharides (e.g., polysialic acid), polyamino acids (e.g., polyglutamic acid, polylysine), polyphosphoric acids, polyamines and derivatives thereof. Exemplary poly(alkylene oxides) include polyethylene glycol (PEG) and polypropylene glycol (PPG). PEG derivatives include those, in which the terminal hydroxyl group is replaced with another moiety, such as an alkyl group (e.g., methyl, ethyl or propyl). In one example, the hydrophilic moiety is methyl-PEG (mPEG).

PEG is usually a mixture of oligomers characterized by an average molecular weight. In one example, the PEG has an average molecular weight from about 200 to about 5000. In another aspect, PEG has an average molecular weight from about 500 to about 1500. In another aspect, PEG has an average molecular weight from about 500 to about 800 or about 900 to about 1200. In one example, the PEG is PEG-600 or is PEG-750. Both linear and branched PEG moieties can be used as the hydrophilic moiety of the solubilizing agent in the practice of the invention. In one aspect, PEG has between 1000 and 5000 subunits. In one aspect, the PEG is PEG 1000. In another aspect, PEG has between 100 and 500 subunits. In yet another aspect, PEG has between 10 and 50 subunits. In one aspect, PEG has between 1 and 25 subunits. In another aspect, PEG has between 15 and 25 subunits. PEG has between 5 and 100 subunits. In another aspect, PEG has between 1 and 500 subunits.

In one aspect, the ratio of the natural and non-natural omega-fatty acids (e.g., omega-3-, omega-6- or omega-9-fatty acids and their esters) to the solubilizing agent is from about 1:0.1 (w/w), about 1:0.3, or a range of about 1:0.3 (w/w) to about 1:20 (w/w); or from about 1:1 (w/w) to about 1:20 (w/w), from about 1:1 (w/w) to about 1:10 (w/w); from about 1:1.3 (w/w) to about 1:5 (w/w), from about 1:2 (w/w) to about 1:4 (w/w), or is about 1:3 (w/w). In another variation, the ratio of the omega-3-fatty acids to the solubilizing agent is from about 1:0.1 (w/w) to about 1:0.3 (w/w), about 1:0.3 (w/w) to about 1:1 (w/w), or from about 1:0.5 (w/w) to about 1:2 (w/w).

Water-Soluble Reducing Agent:

Certain fatty acids are known to be unstable toward oxidation, resulting in the formation of unstable hydroperoxides that break down to different volatile aldehydes that cause an undesirable odor and rancid taste. Microencapsulation using spray dry emulsions and complex coacervation technologies have been used to stabilize fatty acids for use in food products, but such methods do not provide stable aqueous formulations. C. J. Barrow et al, Lipid Technology, May 2007, Vol. 19, No. 5, 108-111. In one embodiment, the water-soluble reducing agent contained in the formulation (e.g., aqueous formulation) protects the lipophilic bioactive molecule from chemical degradation (e.g., oxidative and/or light-induced processes). For example, addition of vitamin C, a water-soluble vitamin C derivative, or a water-insoluble version of vitamin C to a formulation containing DHA/EPA and TPGS serve to prolong the chemical stability of omega-3s in the aqueous formulation for at least several weeks. In other embodiments, the water-soluble reducing agent (e.g. based on vitamin C) is added to the formulation in an amount sufficient to both reduce and stabilize the lipophilic bioactive molecule after reduction. For example, the omega-3-fatty acids and a solution of a solubilizing agent in water (e.g., TPGS, TPGS-1000 or TWEEN-85) are mixed. Upon mixing of the components, micelles of a small particle size are formed (e.g., average particle size between about 10 and about 30 nm). A water-soluble reducing agent, such as vitamin C or a vitamin C derivative, is then added. Excess of water-soluble reducing agent serves to protect against omega-3-fatty acids degradation (e.g., oxidation). In this function, the water-soluble reducing agent can be considered a stabilizer. In one example, the reducing agent is added in an over-stoichiometric mole ratio with respect to the omega-3-fatty acids (e.g., omega-3-, omega-6- or omega-9-fatty acids). In another embodiment, the ratio of omega-3-fatty acids to water-soluble reducing agent in the formulation is between about 100:1 and about 1:20 (w/w), or between about 50:1 and about 1:10 (w/w), or between about 20:1 and about 1:10 (w/w), or between about 10:1 and about 1:10 (w/w), or between about 1:1 (w/w) and about 1:10 (w/w), between about 1:1 and about 1:8 (w/w), about 1:1 and about 1:6 (w/w) or between about 1:1 and about 1:4 (w/w). In yet another embodiment, the ratio of omega-3-fatty acids to water-soluble reducing agent in the formulation is between about 1:1 and about 1:3 (w/w), or between about 1:1 and about 1:2 (w/w). A person of skill in the art will understand that at least part of the reducing agent can be present in its "oxidized" form. For example, when vitamin C is used as the water-soluble reducing agent, at least part of the vitamin C can be present in the formulation as dehydroascorbic acid. In one example, the ratio of omega-fatty acids to water-soluble reducing agent in the formulation is between about 100:1 and about 10:1 (w/w).

In one example according to any of the above embodiments, the omega-fatty acids in the formulation are essentially stable to chemical degradation (e.g., oxidation). In one example, the formulation is essentially stable for at least 30, 60, 90, 120, 160, 180 days, or at least about 6 months, 9 months or about 12 months when stored at a temperature below about 25° C. (e.g., about 4° C. or about 10° C.). Typically, the formulations are stored at about 4° C. At this temperature, the formulations are typically stable for at least 4, 5, 6 or 12 months. In one example, according to any of the above embodiments the formulation is contained in a soft-gelatin capsule. A person of skill will understand that formulations suitable for incorporation into soft-gelatin capsules typically contain less than about 5%, less than about 4%, less than about 3% and less than about 2% (w/w) of water. Hence, in one example, the formulation includes less than 5% (w/w) of water.

The lipophilic bioactive molecule in the above formulations can be any lipophilic bioactive molecule. In one example, according to any of the above embodiments, the lipophilic bioactive molecule is selected from omega-fatty acids (e.g., docosahexaenoic acid (DHA), eicosapentaenoic acid (EPA) and alpha-linolenic acid (ALA)), omega-6-fatty acid, omega-9-fatty acid, carotenoids, essential oils, flavor oils and lipophilic vitamins. Exemplary carotenoids include lutein, astaxanthin, lycopene, fucoxanthin and canthaxanthin.

In one example, according to any of the above embodiments, the formulation is an aqueous formulation and includes at least about 5% (w/w) of water, at least about 10%, at least about 20%, at least about 30%, at least about 40% or at least about 50% (w/w) of water. In another example, the aqueous formulation includes more than 50% (w/w) of water. For example, the aqueous formulation includes at least about 55%, at least about 60%, at least about 65%, at least about 70%, at least about 75% or at least about 80% (w/w) of water. In a further example, the aqueous formulation includes more than 80% (w/w) water. For example, the aqueous formulation includes at least about 85%, at least about 90%, at least about 92%, at least about 94% or at least about 96% (w/w) of water.

In one example, the omega-fatty acids are solubilized in the aqueous formulation through the formation of micelles that are generated most commonly by the self-aggregation of surfactant molecules, or alternatively, by inclusion of the bioactive as part of the micelar array; i.e., mixed micelles formed between the omega-fatty acids and the solubilizing agent. The particle size of the formed micelles in solution may be measured using a dynamic light scattering (DLS) detector.

In one embodiment, the aqueous formulation of the present application is essentially clear (e.g., free of visible precipitation, cloudiness or haziness). In another example, the omega-fatty acids of the present application are formulated with TPGS resulting in an aqueous formulation that, likewise, is essentially clear. Clear formulations of the present application can be colored. In one example, the formulation is essentially clear when the micelles have a particle size below the visible size (e.g., below 150 nm). Hence, in another exemplary embodiment, the micelles formed by the solubilizing agent containing the omega-fatty acids have a median (average) particle size of less than about 100 nm. In another example, the micelles formed between the omega-fatty acids and the solubilizing agent, have a median particle size of less than about 90 nm, less than about 80 nm, less than about 70 nm or less than about 60 nm. In a further example, the micelles formed between the omega-fatty acids and the solubilizing agent, have a median particle size of less than about 50 nm, less than about 40 nm or less than about 30 nm. In another exemplary embodiment, the average particle size is from about 7 nm to about 90 nm. Another exemplary average particle size is from about 5 nm to about 70 nm, from about 10 nm to about 50 nm, from about 10 nm to about 30 nm, or from about 7 nm to about 10 nm. In a particular example, the micelles formed between the omega-fatty acids and the solubilizing agent, have a median particle size between about 30 nm and about 10 nm (e.g., about 25 nm).

In another example, the aqueous formulation does not include an alcoholic solvent, although such inclusion is possible when part of the solubilizing agent (e.g., as in Cremophore, which contains ethanol). Exemplary alcoholic solvents include solvents, such as ethanol, methanol, propanol, butanol and higher alcohols (e.g., $C_5$-$C_{20}$ alcohols). Alcoholic solvents also include polyhydric alcohols, such as ethylene glycol, propylene glycol, glycerol and the like. The term "alcoholic solvent" does not include polymers, such as polymeric versions of the above listed polyhydric alcohols (e.g., poly(alkylene oxides)), such as PEG or PPG).

In one example, according to any of the above embodiments, the concentration of omega-fatty acids in the formulation is at least about 20 mg/mL and can be as high as about 60, about 80, about 100 or more than about 100 mg/mL. In one example, the concentration of omega-fatty acids in the aqueous formulation of the present application is at least about 1 mg/mL, at least about 5 mg/mL, at least about 10 mg/mL, at least about 20 mg/mL, at least about 30 mg/mL, at least about 40 mg/mL, at least about 50 mg/mL, at least about 60 mg/mL, at least about 70 mg/mL or at least about 80 mg/mL, at least about 85 mg/mL, at least about 90 mg/mL, at least about 95 mg/mL or at least about 100 mg/mL, at least about 110 mg/mL, at least about 120 mg/mL, at least about 130 mg/mL, at least about 140 mg/mL, at least about 150 mg/mL, at least about 160 mg/mL, at least about 170 mg/mL, at least about 180 mg/mL, at least about 190 mg/mL or at least about 200 mg/mL. In another example, the concentration of omega-fatty acids in the aqueous formulation is greater than 200 mg/mL.

In one embodiment, the present application provides a water-soluble formulation comprising bioactive agent or mixtures of bioactive agents as disclosed herein, a water-soluble reducing and/or antioxidizing agent, water-insoluble reducing and/or antioxidizing agent, a solubilizing agent, a metal chelating agent, and a bisulfite salt or a metabisulfite salt. In another embodiment, the present application provides a water-soluble formulation comprising omega-fatty acids, a water-soluble antioxidant and/or reducing agent, a solubilizing agent, a metal chelating agent, and a bisulfite salt or a metabisulfite salt. In one aspect, the chelating agent is EDTA and the bisulfite salt is sodium bisulfite. In one example, the solubilizing agent has a structure according to Formula (I) described herein.

In particular variations of each of the above aspects and embodiments, the formulation may comprise the natural and non-natural omega-fatty acids and TPGS-1000; natural, non-natural and synthetic surfactants and mixtures of surfactants, including, for example, two or more surfactants of differing structural types (e.g., TPGS-1000 and Tween-80), two or more surfactants from within the same structural class (e.g., TPGS-1000+TPGS-600). In another variation of the above formulations, the formulations may also comprise any of the above combinations as their free alcohols, or as their ether or ester derivatives (of their PEG portion). In another particular variation of the above formulations, the formulations may also comprise antioxidants that are lipophilic in nature (e.g., vitamin C palmitate), hydrophilic in nature (e.g., vitamin C), and any combinations of these, including more than one of each in any formulations. In another particular variation of the above formulations, the formulations may also comprise chelating agents that are lipophilic in nature, hydrophilic in nature (e.g., EDTA, HEDTA, DTPA and NTA), and any combinations of these, and in any number (i.e., more than one of each in any formulation) or ratio. In another particular variation of the above formulations, the formulations may also comprise salts such as salts that are lipophilic in nature (e.g., ammonium salts, such as $R_4N^+X^-$), hydrophilic in nature (e.g., $NaHSO_3$), and any combinations of these, and in any number (i.e., more than one of each in any formulation) or ratio, that may vary with each application. According to the present formulations, variations of each of the above natural and non-natural omega-fatty acids and their esters, the surfactants, the antioxidants, chelating agents, lipophilic and hydrophilic salts, and each of these elements and their combinations, may be used to provide the stable, water soluble bioactive agents such as the omega-fatty acids formulations of the present application.

In one example according to any of the above embodiments, the bioactive agent, mixtures of bioactive agents, or omega-fatty acids formulation is essentially stable to chemical degradation. In one example, the omega-fatty acids is essentially stable for at least 30, 60, 180 days, or at least 6 months, 9 months or 12 months, when stored at a temperature below about 25° C. (e.g., about 4° C. or about 10° C.). Typically, omega-fatty acids formulations are stored at about 4° C. At this temperature, the omega-fatty acids formulations are stable for at least 90 days, at least 6 months or at least 12 months.

Another advantage of the above omega-fatty acids formulations is that they can be light in color or substantially colorless. The lighter color can be more appealing to the consumer and provides a greater flexibility with respect to the use of coloring agents and other additives. Another advantage of the current formulations stems from the fact that they combine at least two beneficial ingredients (omega-fatty acids and vitamin C/vitamin C derivative) in a single preparation. This can provide greater convenience to a consumer. When TPGS or TPGS-1000 is used as the solubilizing agent, the formulations disclosed herein provide a combination of at least three beneficial ingredients (omega-fatty acids, vitamin C/vitamin C derivative and vitamin E) in a single preparation. In another example, the omega-fatty acids are emulsified in the formulation in the form of micelles that include the omega-fatty acids and the solubilizing agent. In a typical emulsion of the present application, the micelles are small in size, and are between about 10 and about 30 nm. In another example, the small size of the micelles causes the emulsion to be essentially clear in appearance even at high compound concentrations (e.g., 40, 60, 80 or 100 mg/mL). In one example, the omega-fatty acids concentration in the aqueous formulations of the present application is at least about 20 mg/mL and can be as high as about 60, about 80, about 100 or more than about 100 mg/mL.

Beverages:

In another example, the present application provides a mixture between a formulation of the present application (e.g., a water-soluble formulation) and an original beverage to create a beverage of the present application. The original beverage can be any beverage (e.g., a clear beverage). Exemplary original beverages are described herein and include carbonated or non-carbonated waters, flavored waters, soft drinks and the like. In one example, the mixture (beverage of the present application) includes between about 1 mg/L and about 1000 mg/L of solubilized omega-fatty acids. In another example, the mixture includes between about 10 mg/L and about 500 mg/L of solubilized omega-fatty acids, between about 10 mg/L and about 450 mg/mL, between about 10 mg/L and about 400 mg/mL, between about 10 mg/L and about 350 mg/mL, between about 10 mg/L and about 300 mg/mL, or between about 10 mg/L and about 250 mg/mL of solubilized omega-fatty acids. In a further example, the mixture includes between about 20 mg/L and about 250 mg/L, between about 20 mg/L and about 200 mg/mL, between about 20 mg/L and about 150 mg/mL, between about 20 mg/L and about 100 mg/mL, or between about 20 mg/L and about 80 mg/mL, between about 20 mg/L and about 60 mg/mL, between about 20 mg/L and about 40 mg/mL of solubilized omega-fatty acids. According, in one aspect, the beverage may comprise of about 1,000 mg or less of solubilized omega-fatty acids. In another aspect, the beverage may comprise of about 500 mg or less of solubilized omega-fatty acids. In another aspect, the beverage may comprise of about 250 mg or less of solubilized omega-fatty acids. In one aspect, the beverage may comprise of a range of about 10 mg to about 500 mg per serving. In another aspect, the beverage may comprise of a range of about 25 mg to about 500 mg per serving. In certain aspects, the beverage may have two servings. In certain variation of the beverage, the beverage may comprise about 15% to about 30% of the daily recommended value of the omega-fatty acids.

In one embodiment, the concentration of the omega-3 fatty acids in the formulation provides the daily recommended dose for omega-3 fatty acids. In one aspect, the formulation provides up to about 500 mg of omega-3 fatty acids per serving.

In a particular example according to any of the above embodiments, the present application provides a mixture between omega-fatty acids formulation of the present application (e.g., an aqueous omega-fatty acids formulation) and an original beverage (e.g., carbonated or non-carbonated water) to form an omega-fatty acids beverage. In another aspect, the present application provides a non-alcoholic beverage comprising (a) solubilized omega-fatty acids (e.g., omega-3-fatty acids-50), (b) a water-soluble reducing agent of the present application (e.g., vitamin C), (c) a solubilizing agent, (d) a metal chelating agent, and (e) sodium bisulfite.

In another embodiment, the omega-fatty acids beverage contains between about 1 mg/L and about 1000 mg/L of solubilized omega-fatty acids, between about 10 mg/L and about 500 mg/L of solubilized omega-fatty acids, between about 10 mg/L and about 450 mg/mL, between about 10 mg/L and about 400 mg/mL, between about 10 mg/L and about 350 mg/mL, between about 10 mg/L and about 300 mg/mL, or between about 10 mg/L and about 250 mg/mL of solubilized omega-fatty acids. In a further example, the mixture includes between about 20 mg/L and about 250 mg/L, between about 20 mg/L and about 200 mg/mL, between about 20 mg/L and about 150 mg/mL, between about 20 mg/L and about 100 mg/mL, or between about 20 mg/L and about 80 mg/mL, between about 20 mg/L and about 60 mg/mL, between about 20 mg/L and about 40 mg/mL of solubilized omega-fatty acids.

In a further example according to any of the above embodiments, the beverage further includes a coloring agent and/or a flavoring agent. It is possible to add one or more fruit and/or vegetable juice concentrates and/or flavor improvers to the beverage. For example, a mixture of about LIMETTE citrus (e.g., about 1.38 g/l), cassis (e.g., about 1.04 g/l), mango (e.g., about 1.04 g/l) or combinations thereof, can be added to the beverage. In another example, maltodextrin (e.g., about 20 g/l), fructose (e.g., about 50 g/l) or combinations thereof can be added to the beverage. In another example, the finished beverage is subjected to a primary and, optionally, a secondary filtration.

In yet another example according to any of the above embodiments, the omega-fatty acids can be solubilized and stabilized in the beverage. For example, the beverage is essentially free of omega-fatty acids precipitation. Hence, in another example, the beverage is essentially clear. Clarity of a beverage can be assessed using turbidity measurements. In one example, the turbidity of the omega-fatty acids beverage is comparable (e.g., not more than 5 times) of the turbidity of the control beverage. In one example, the turbidity of the omega-fatty acids beverage is not more than about 500%, not more than about 400%, not more than about 300% or not more than about 200% higher than the turbidity of the control. In yet another example, the turbidity is not more than about 180%, not more than about 160%, not more than about 140%, not more than about 120% or not more than about 100% higher than the turbidity of the control. The turbidity is 100% higher than the control, when the turbidity of the beverage is twice as high as the turbidity of the control.

In another example, the turbidity of the omega-fatty acids beverage is stable over time. For example, the turbidity of the beverage is stable over a period of at least 60 days, at least 90 days, or at least 180 days when the beverage is stored at ambient temperature (e.g., below about 25° C.). After production, the beverage can be packaged into opaque containers which are, in particular, opaque to light, such as visible light and near and far ultraviolet light. It is also possible to use for this purpose containers, for example, cans which cover the entire spectrum of light. Cans made of aluminum or aluminum alloys are preferably used. It is also possible to accommodate the beverage according to the present application in metal foil or aluminum foil sachets. In another example, the beverage is packaged in Tetrapak containers.

In addition, the beverage can be enriched with vitamins. In one example, the beverage includes at least one B vitamin. Exemplary B-vitamins include vitamin B1, vitamin B2, vitamin B3, vitamin B5, vitamin B6 and vitamin B12. In another example, the beverage includes vitamin E. In one example, the vitamin is first formulated into an aqueous composition, which is subsequently added to the beverage. The solubilizing agent used to solubilize the vitamin can be the same solubilizing agent used to solubilize the omega-fatty acids.

Lipophilic Bioactive Molecule:

The bioactive molecule of the present application can be any lipophilic molecule. In one example, the lipophilic bioactive molecule is selected from compounds with a water-solubility that can be increased using a solubilizing agent of the present application. In another example, the bioactive lipophilic molecule is a molecule associated with pharmaceutical or neutraceutical value. The term "lipophilic bioactive molecule" includes derivatives of such molecules (e.g., esters or amides thereof) and combinations thereof. For example, the lipophilic bioactive molecule has at least one free OH or COOH group, which can be converted to an ester group. In another example, the lipophilic bioactive molecule has at least one free primary or secondary amino group, which can be converted to an amide or related derivatives (e.g, sulfonamides, carbamates, etc.).

Oils, Fats and Fatty Acids:

In another embodiment, the lipophilic bioactive molecule is an oil or an oil component. The term "oil" includes oils derived from plant material, such as seed oils, algae oils, essential oils, oils derived from animals, such as fish or marine oils (e.g., salmon oil, cod liver oil, sardine oil, anchovie oil, haik oil, polack oil, manhadon oil, krill oil) and other fats. In one example, the oil has food grade. Exemplary oils derived from plant materials include flaxseed oil, borage seed oil, garlic oil, pumpkin seed oil, evening primrose oil, wheat germ oil, saw palmetto berry oil, canola oil, vegetable oil, safflower oil, sunflower oil, nasturtium seed oil, mustard seed oil, olive oil, sesame oil, soybean oil, corn oil, peanut oil, cottonseed oil, rice bran oil, babassu nut oil, palm oil, low erucic rapeseed oil, palm kernel oil, lupin oil, coconut oil, jojoba oil and shea butter. Exemplary essential oils include citrus oils, bergamot oil, jasmine oil, ylang ylang oil, rosemary oil, cinnamon oil, lavender oil, rose oil, rose geranium oil, patchouli oil, neroli oil, vetiver oil and the like. The term essential oil also includes fragrances and flavoring oils (e.g., fruit flavor oils, citrus flavor, almond flavor). Exemplary oils derived from animals include animal fats, such as tallow (e.g., beef tallow), butter, chicken fat, lard, dairy butterfat, or combinations thereof. In another exemplary embodiment, the lipophilic bioactive molecule is selected from an oil comprising at least one fatty acids (e.g., an essential fatty acid). In another exemplary embodiment, the lipophilic bioactive molecule is selected from an oil comprising at least one type of an omega-3 fatty acids, an oil comprising at least one type of an omega-6 fatty acids, an oil comprising at least one type of an omega-9 fatty acid and an oil comprising at least one type of an omega-12 fatty acid. Exemplary types of omega-3 fatty acid, omega-6 fatty acid, omega-9 fatty acid and omega-12 fatty acid are disclosed herein. In another embodiment, the lipophilic bioactive molecule is selected from the group consisting of an omega-3 fatty acid, an omega-6 fatty acid, an omega-9 fatty acid, and an omega-12 fatty acid. In another embodiment, the lipophilic bioactive molecule is an essential fatty acid (EFA), such as a linolenic acid. In another exemplary embodiment, the lipophilic bioactive molecule is an omega-3 unsaturated fatty acid, such as alpha-linolenic acid (ALA), docosahexaenoic acid (DHA), eicosapentaenoic acid (EPA), stearidonic acid, eicosatetraenoic acid and docosapentaenoic acid. In another exemplary embodiment, the lipophilic bioactive molecule is an omega-6 unsaturated fatty acid, such as linoleic acid, gamma-linolenic acid and arachidonic acid. In yet another exemplary embodiment, the lipophilic bioactive molecule is an omega-9 unsaturated fatty acid, such as oleic acid, eicosenoic acid and erucic acid, as well as conjugated linoleic acid (CLA). In a further exemplary embodiment, the lipophilic bioactive molecule is an omega-12 unsaturated fatty acid. The term "fatty acid" also includes any derivative of those compounds, such as mixed triglycerides, diglyceride esters and alkyl esters, such as methyl- and ethyl esters. In one aspect, the omega fatty acids of the present application include the triglyceride esters. Additional fatty acids of the present application are summarized below.

Exemplary Omega-3, Omega-6 and Omega-9 Fatty Acids Common Name Lipid Name Chemical Name Omega-3 Fatty Acids: α-Linolenic acid (ALA), stearidonic acid; eicosatetraenoic acid; eicosapentaenoic acid (EPA), docosapentaenoic acid, docosahexaenoic acid (DHA); Omega-6 Fatty Acids: Linoleic acid, gamma-linolenic acid, eicosadienoic acid, dihomo-gamma-linolenic acid, arachidonic acid, docosadienoic acid, adrenic acid, docosapentaenoic acid; Omega-9 Fatty Acids: Oleic acid, eicosenoic acid, mead acid, erucic acid, nervonic acid.

In another exemplary embodiment, the lipophilic bioactive molecule is a botanical extract or a component thereof. Exemplary extracts include extracts of ginseng, hawthorne, St. John's wort, valerian, black cohosh, yohimbe, ephedra, red clover, cayenne, echinacea, arnica (e.g., arnica montana), grape seeds, kava kava, bilberry, gingko biloba, green tea, wine leaf, Japanese knotwood and any other botanical extract available as a dietary supplement.

In one example, the formulation includes from about 0.01% (w/w) to about 0.1% (w/w) of an omega-fatty acids, from about 0.01% (w/w) to about 0.5% (w/w), from about 0.01% (w/w) to about 1% (w/w), from about 0.05% (w/w) to about 0.25% (w/w), from about 0.1% (w/w) to about 1% (w/w), from about 0.1% (w/w) to about 0.75% (w/w), from about 1% (w/w) to about 3% (w/w), from about 1% (w/w) to about 10% (w/w), from about 1% (w/w) to about 20% (w/w), from about 1% (w/w) to about 30% (w/w), from about 1% (w/w) to about 40% (w/w), from about 5% to about 50% by weight, or from about 10% to about 30% (w/w), for example, from about 15% to about 25% (w/w).

Solubilizing Agents Wherein Z is a Tocopherol or a Tocotrienol:

In another embodiment, Z is selected from a substituted or unsubstituted tocopherol and a substituted or unsubstituted tocotrienol. In one example, Z is an α-, β-, γ-, or δ-tocopherol. α-(+)-Tocopherol (natural) and α-(±)-tocopherol (synthetic) are preferred tocopherols, with synthetic racemic tocopherol being particularly preferred for TPGS. In another embodiment, Z has a structure according to the following formula:

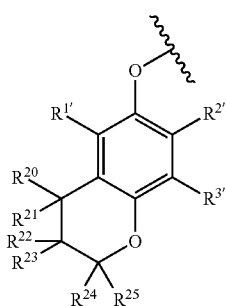

wherein $R^{1'}$, $R^{2'}$ and $R^{3'}$ are independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{2'}$ and $R^{3'}$, together with the carbon atoms to which they are attached, are optionally joined to form a 5- to 7-membered ring. $R^{20}$, $R^{21}$, $R^{22}$, $R^{23}$, $R^{24}$ and $R^{25}$ are selected from H, halogen, nitro, cyano, $OR^{17}$, $SR^{17}$, $NR^{17}R^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In another embodiment, at least one of $R^{24}$ and $R^{25}$ comprises an isoprene moiety. In another embodiment, $R^{1'}$, $R^{2'}$ and $R^{3'}$ are independently selected from H and methyl. In another exemplary embodiment, $R^{3'}$ is methyl, $R^{2'}$ is methyl and $R^{1'}$ is methyl. In another exemplary embodiment, $R^{3'}$ is H and $R^{1'}$ is methyl. In another exemplary embodiment, $R^{3'}$ is methyl, $R^{2'}$ is methyl and $R^{1'}$ is H. In another exemplary embodiment, $R^{3'}$ is methyl, $R^{2'}$ is H and $R^{1'}$ is H.

In one example, Z has a structure according to the following formulae:

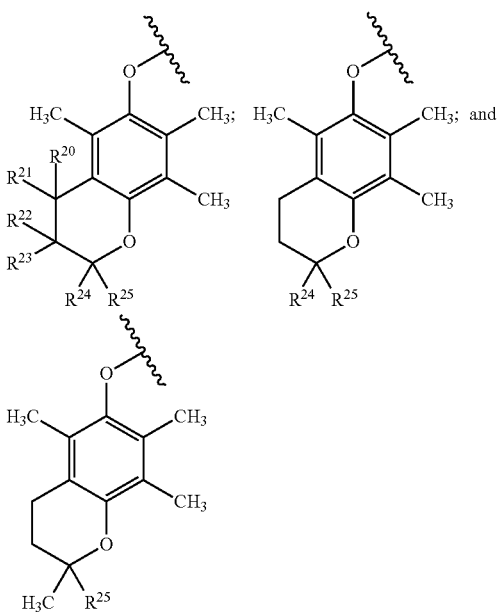

wherein $R^{25}$ is selected from substituted or unsubstituted alkyl and substituted or unsubstituted heteroalkyl. In one example, $R^{24}$ is methyl. In another example, $R^{25}$ includes a moiety having a structure selected from the following formulae:

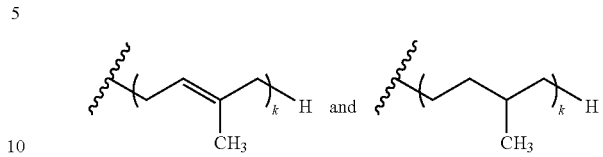

wherein k is an integer selected from 1 to 12. In another embodiment, k is from 2 to 6. In another exemplary embodiment, k is 3.

In another embodiment, the solubilizing agent has a structure according to the following formula:

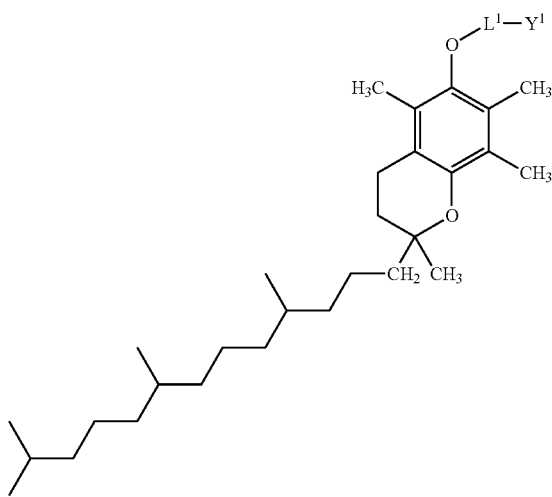

In another embodiment, the moiety $L^1$-$Y^1$ has a structure according to the following formula:

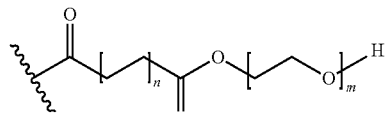

wherein n is selected from 1 to 20, m is selected from 1 to 5000. In another embodiment, n is 4. In another embodiment, m is a selected from 1 to 2,500.

Methods of making the above solubilizing agents are known in the art as disclosed in U.S. Pat. Nos. 6,045,826, 6,191,172, 6,632,443 and WO 96/17626, all herein incorporated by reference in their entirety. Similarly, TPGS may be prepared accordingly, or by using succinic anhydride as the linker in place of the diacid chloride as precursor to the four-carbon linker.

Specific Sterols and Linkers:

In another embodiment, the solubilizing agent has a structure, which is a member selected from:

Specific Tocopherols and Linkers:

In another embodiment, the solubilizing agent has a structure according to one of the following formulae:

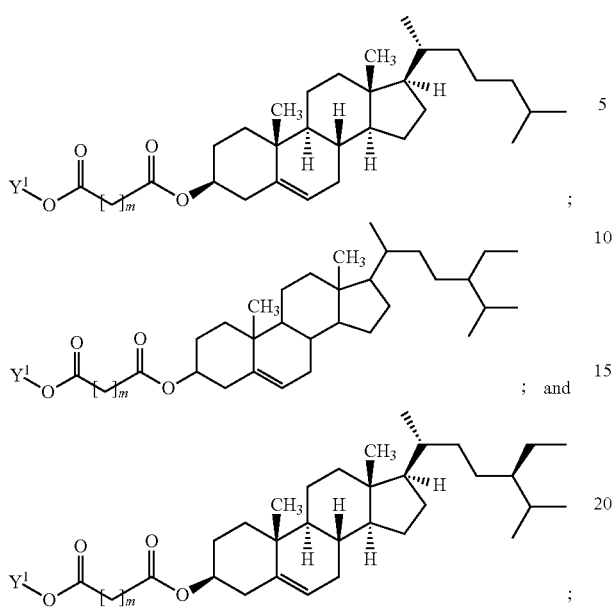

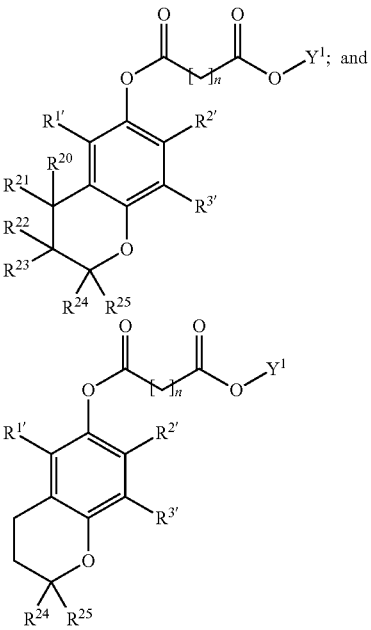

wherein m is selected from 2-16. In one example, m is selected from 2, 6, 8, 10, 12 and 14. In another example, m is 2. In yet another example, m is 8.

Specific Sterols and PEG:

In another embodiment, the solubilizing agent is selected from

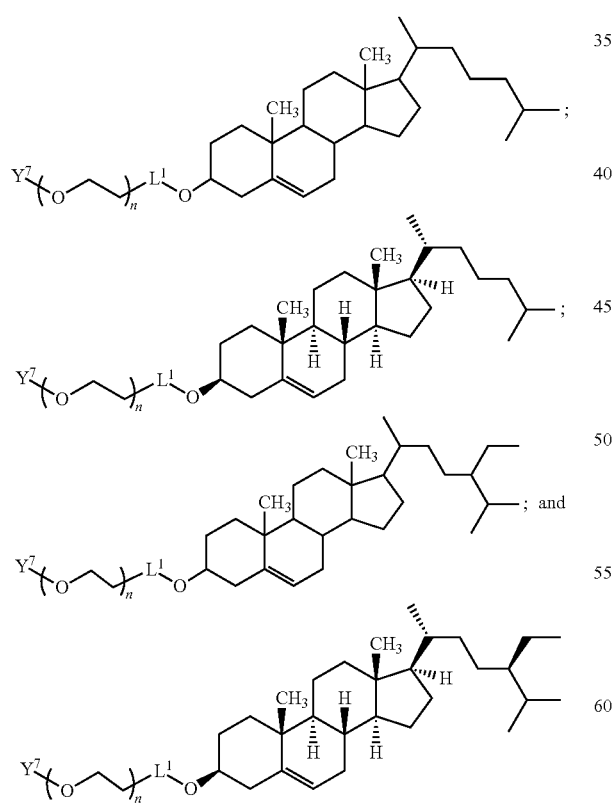

wherein n is selected from 10 to 2500, $L^1$ is a linker moiety, $Y^7$ is selected from H and methyl.

wherein n is an integer selected from 1 to 20. $Y^1$, $R^{1'}$, $R^{2'}$, $R^{3'}$, $R^{20}$, $R^{21}$, $R^{22}$, $R^{23}$, $R^{24}$ and $R^{25}$ are defined as herein above.

Specific Tocopherols and PEG:

In another embodiment, the solubilizing agent has a structure according to the following formula:

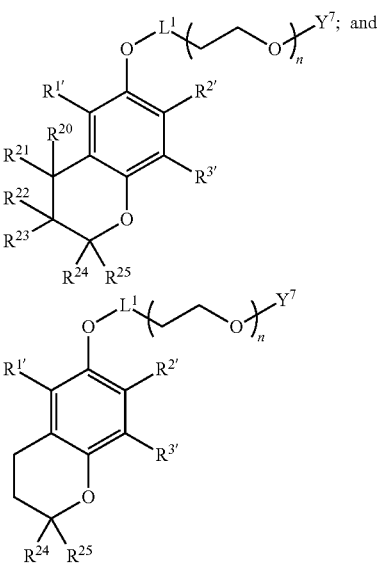

wherein n is a member selected from 10 to 2500. $L^1$, $R^{1'}$, $R^{2'}$, $R^{3'}$, $R^{20}$, $R^{21}$, $R^{22}$, $R^{23}$, $R^{24}$ and $R^{25}$ are defined as herein above. $Y^7$ is selected from H and methyl.

In another embodiment, the formulations of the present application include from about 10% to about 50% by weight of a solubilizing agent, such as TPGS or TPGS-1000. The formulations include from about 15% to about 40% (w/w)

solubilizing agent, from about 20% to about 40% (w/w), and from about 20 to about 35% (w/w). In another embodiment, the present application includes from about 0.01% (w/w) to about 5% (w/w), from about 0.01% (w/w) to about 0.1% (w/w), from about 0.01% (w/w) to about 1% (w/w), from about 0.1% (w/w) to about 1% (w/w), from about 0.1% (w/w) to about 0.75% (w/w), 1% (w/w) to about 3% (w/w), and from about 0.05% (w/w) to about 0.25% (w/w) of a solubilizing agent.

The soft gel capsules of the present application (based on a soft gel capsule weight of from about 900 mg to about 1200 mg) include a solubilizing agent from about 1% to about 30% by weight. In one embodiment, the soft gel capsule includes from about 5% to about 30% (w/w), from about 8% to about 20% of a solubilizing agent, such as TPGS or TPGS-1000.

Water-Soluble Reducing Agent:

In another embodiment, the water-soluble reducing agent is vitamin C, a water-soluble vitamin C derivative (e.g., a salt), or a combination thereof. In one embodiment, the compositions of the present application are selected from ascorbic acid (vitamin C), a vitamin C derivatives, salts thereof and combinations thereof. In one embodiment, the vitamin C salt, or salt of a vitamin C derivative is an edible (e.g., pharmaceutically acceptable) salt, such as a calcium, sodium, magnesium, potassium and zinc salt. Mixed salts of vitamin C or a vitamin C derivative are also within the scope of the present application. The compositions may include one or more vitamin C derivative. The vitamin C derivative can be any analog of vitamin C. Exemplary vitamin C derivative include those in which at least one of the hydroxyl groups of the ascorbic acid molecule (e.g., 2-OH, 3-OH, 5-OH, 6-OH) is derivatized with a modifying group (see e.g., U.S. Pat. No. 5,078,989 to Ando et al.). Alternatively one or more of the hydroxyl group can be substituted with another moiety. In another embodiment, the compositions may include vitamin C as well as at least one vitamin C derivative.

In order to exhibit stabilizer activity in vitro, the vitamin C derivative can include a free 2-OH and a free 3-OH group. In one embodiment, the composition may include at least one vitamin C derivative, in which both the 2-OH and the 3-OH group are non-functionalized. Exemplary vitamin C derivatives according to this embodiment include esters of ascorbic acid, wherein at least one of the 5-OH and the 6-OH group is derivatized.

Exemplary vitamin C derivatives according to this embodiment include esters, such as 6-O-octanoyl-ascorbic acid, 6-O-dodecanoyl-ascorbic acid, 6-O-tetradecanoyl-ascorbic acid, 6-O-octadecanoyl-ascorbic acid, 6-O-dodecanedioyl-ascorbic acid, 6-O-docosanedioyl-ascorbic acid, 6-O-thapsoyl-ascorbic acid, 6-O-suberoyl-ascorbic acid, 6-O-adipoyl-ascorbic acid. Other examples include those esters, in which the lipophilic part of the molecule represents a mono- or polyunsaturated fatty acid. In one embodiment, the unsaturated fatty acids is an essential fatty acids associated with a health benefit (e.g., human health), such as an omega-3 (alpha-linolenic acid), omega-6 or omega-9 fatty acid. Other examples include esters of vitamin C including an amino acid residue. In another embodiment, the compositions of the present application include 2-O-alkyl or 3-O-alkyl derivatives of vitamin C. 3-O-alkyl-ascorbic acids have been reported by Nihro et al., Chem. Pharm. Bull. 1991, 39: 1731-1735, the disclosure of which is incorporated herein by reference. In yet another embodiment, the vitamin C derivative is a glucoside of ascorbic acid, such as ascorbic acid 1-glucoside, ascorbic acid 2-glucoside, ascorbic acid 3-glucoside, ascorbic acid 5-glucoside, and ascorbic acid 6-glucoside. Examples include 2-O-(alpha-D-glucopyranosyl)-ascorbic acid (see e.g., U.S. Pat. No. 5,137,723) and 2-O-(beta-D-glucopyranosyl)-ascorbic acid (see e.g., U.S. Patent Application No. 2005/0113312). Also within the scope of the present application are difunctionalized derivatives of vitamin C, such as e.g., 6-O-acyl-2-O-(alpha-D-glucopyranosyl) ascorbic acids (see e.g., Yamamoto et al., J. Med. Chem. 2002, 45(2): 462-468. The above references are incorporated herein by reference. In a further embodiment, the vitamin C derivative is a phosphate of ascorbic acid. In another embodiment the ascorbyl phosphate is a salt of an alkali metal, an alkaline earth metal, or a transition metal. Preferred examples include magnesium ascorbyl phosphate, sodium ascorbyl phosphate (e.g., sodium salt of ascorbyl-2-monophosphate), calcium ascorbyl phosphate, potassium ascorbyl phosphate and mixed salts, such as e.g., sodium magnesium ascorbyl phosphate or sodium calcium ascorbyl phosphate, aminopropyl ascorbyl phosphate. The ascorbyl phosphate can exist as a hydrate, wherein dihydrates are common. An exemplary dihydrate is available for example from DSM under the product name STAY-C 50.

In another embodiment, the stabilizer is in excess in relation to the omega-fatty acids, or the omega-fatty acid is in excess of the stabilizer. In another exemplary embodiment, the ratio of the omega-fatty acids to the stabilizer is from about 1:1 (w/w) to about 1:6 (w/w), from about 1:1 (w/w) to about 1:5 (w/w), from about 1:1.3 (w/w) to about 1:3 (w/w), from about 1:2 (w/w) to about 1:4 (w/w), or about 1:3 (w/w). In another embodiment, the ratio of the stabilizer to the omega-fatty acid is from about 1:1 (w/w) to about 1:6 (w/w), from about 1:1 (w/w) to about 1:5 (w/w), from about 1:1.3 (w/w) to about 1:3 (w/w), from about 1:2 (w/w) to about 1:4 (w/w), or about 1:3 (w/w).

In another embodiment, the stabilizer is vitamin C or a vitamin C derivative. In one example, the vitamin C or the vitamin C derivative is used in a molar excess in relation to the lipophilic bioactive molecule. In another exemplary embodiment, the ratio of the lipophilic bioactive molecule to said vitamin C or vitamin C derivative is from about 1:1 (w/w) to about 1:6 (w/w), from about 1:1 (w/w) to about 1:10 (w/w), from about 1:1.3 (w/w) to about 1:5 (w/w), from about 1:2 (w/w) to about 1:4 (w/w), or about 1:3 (w/w).

The Metal Chelating Agent:

In another embodiment, the metal chelator, chelating agent or metal chelating moiety is a chelator that has demonstrated affinity metal ions. Such metal ions include certain metal ions such as iron, but may also include lead, mercury and nickel. In one aspect, the chelator is EDTA or ethylenediaminetetraacetic acid disodium salt dihydrate and the metal ion is iron (II) or iron (III). In one aspect, the metal ion is iron (III). In one embodiment, the formulations of the present application include from about 0.001% to about 0.01% by weight of the chelator relative to the omega-fatty acids (w/w), (i.e. weight of chelator/weight of omega-fatty acids), from about 0.01% to about 0.1%, from about 0.1% to about 0.5%, from about 0.5% to about 1.0%, from about 1.0% to about 2.0%, from about 2.0% to about 4.0%, from about 4.0% to about 6.0%, or about 4% of the chelator relative to the omega-fatty acids. In another embodiment, the formulations of the present application include from about 6.0% to about 10.0% by weight of the chelator relative to the omega-fatty acids (w/w), from 10.0% to about 15%, or from about 15% to about 20% by weight of the chelator relative to the omega-fatty acids.

The Bisulfite Agent:

In one embodiment, the bisulfite agent of the present formulation is a metal bisulfite. In one aspect, the bisulfite agent is sodium bisulfite. The sodium bisulfite will react with any aldehyde present in the formulation to form a bisulfite addition compound and eliminates any undesired aldehyde odors. In one embodiment, the formulations of the present application include from about 0.0001% to about 0.001% by weight of sodium bisulfite relative to the omega-fatty acids (w/w), (i.e. weight of sodium bisulfite/weight of omega-fatty acids), from about 0.001% to about 0.01%, from about 0.01% to about 0.05%, from about 0.05% to about 0.10%, from about 0.10% to about 0.2%, from about 0.2% to about 0.4%, from about 0.4% to about 0.6%, or about 0.5% of sodium bisulfite relative to the omega-fatty acids. In another embodiment, the formulations of the present application include from about 0.6% to about 1.0% by weight of the chelator relative to the omega-fatty acids (w/w), from 1.0% to about 1.5%, or from about 1.5% to about 2.0% by weight of sodium bisulfite relative to the omega-fatty acids. As one skilled in the art would appreciate, compositions comprising the formulation that is known or that is determined to contain larger concentrations of metals, such as iron, will require the use of higher concentrations of the metal bisulfite, and the concentration of the metal bisulfite may be adjusted accordingly.

Other Components:

The formulations described herein (either aqueous or non-aqueous) can further include various ingredients useful to stabilize the composition, promote the bioavailability of the lipophilic bioactive molecule, or provide nutritional value. Exemplary additives of the present formulations include, without limitation, one or more alternative solubilizing agents, pharmaceutical drug molecules, antibiotics, sterols, vitamins, provitamins, carotenoids (e.g., alpha and beta-carotenes, cryptoxanthin, lutein and zeaxanthin), phospholipids, L-carnitine, starches, sugars, fats, stabilizers, reducing agents, free radical scavengers, amino acids, amino acid analogs, proteins, solvents, emulsifiers, adjuvants, sweeteners, fillers, flavoring agents, coloring agents, lubricants, binders, moisturizing agents, preservatives, suspending agents, starch, hydrolyzed starch(es), derivatives thereof and combinations thereof.

In one embodiment, the formulation further comprises gelatin. In another embodiment, the formulation further comprises sorbitol. In another embodiment, the formulation further comprises glycerin, or any ester derivatives therefrom. In another embodiment, the formulation further comprises purified water. In another embodiment, the formulation further comprises polysorbate 80. In yet another embodiment, the formulation further comprises hydroxylated lecitin. In another embodiment, the formulation further comprises medium chain triglycerides. In another embodiment, the formulation further comprises annato seed extract. In another embodiment, the formulation further comprises soybean oil. In another embodiment, the formulation further comprises omega-3 enriched fish oil. In yet another embodiment, the formulation further comprises rice bran oil. In another embodiment, the formulation further comprises carotenoids. In another embodiment, the formulation further comprises titanium dioxide. In another embodiment, the formulation further comprises suspending agents such as silica (silicon dioxide). In another embodiment, the formulation further comprises riboflavin. Various other additives can be incorporated into the present formulations including, without limitation, phospholipids, L-carnitine, anti-inflammatory agents, anti-aging agents, starches, sugars, fats, stabilizers, amino acids, proteins, flavorings, coloring agents, hydrolyzed starch(es) and derivatives thereof (such as time release esters (Ester-C, Ester-E)) or combinations thereof. Anti-inflammatory agents of use in the present application include, but are not limited to, bisabolol, mentholatum, dapsone, aloe, hydrocortisone, and the like. Anti-aging agents of use in the present application include, but are not limited to, niacinamide, retinol and retinoid derivatives, AHA, lipoic acid, beta hydroxy acids, salicylic acid, copper binding peptides and the like.

Vitamin(s) in a unit dosage form of the present application are present in amount ranging from about 5 mg to about 500 mg. More particularly, the vitamin(s) is present in an amount ranging from about 10 mg to about 400 mg. Even more specifically, the vitamin(s) is present from about 250 mg to about 400 mg. Most specifically, the vitamin(s) is present in an amount ranging from about 10 mg to about 50 mg. For example, B vitamins are in usually incorporated in the range of about 1 milligram to about 10 milligrams, i.e., from about 3 micrograms to about 50 micrograms of B12. Folic acid, for example, is generally incorporated in a range of about 50 to about 400 micrograms, biotin is generally incorporated in a range of about 25 to about 700 micrograms and cyanocobalamin is incorporated in a range of about 3 micrograms to about 50 micrograms.

Mineral(s) in a unit dosage form of the present application are present in an amount ranging from about 25 mg to about 1000 mg. More particularly, the mineral(s) are present in the composition ranging from about 25 mg to about 500 mg. Even more particularly, the mineral(s) are present in the composition in an amount ranging from about 100 mg to about 600 mg. In the formulations of the present application the additional components are usually a minor component (from about 0.001% to about 20% by weight or preferably from about 0.01% to about 10% by weight) with the remainder being various vehicles or carriers and processing aids helpful for forming the desired dosing form.

Pharmaceutical Formulations:

According to another aspect, the present application provides pharmaceutical formulations comprising a formulation of the present application and a pharmaceutically acceptable carrier. Pharmaceutical formulations include nutraceutical formulations. An exemplary unit dosage form (e.g., contained in a soft gel capsule) of the present application includes a pharmaceutical grade lipophilic bioactive molecule (e.g., an omega-3-fatty acid, DHA) in an amount of about 1% to about 30% by weight. In one embodiment, the unit dosage form (e.g., soft gel capsule) includes from about 3% to about 20% (w/w), or from about 5% to about 20% of a lipohilic bioactive molecule. Typically, soft-gel formulations include from about 5% to about 30% (w/w) of lipophilic bioactive molecule, from about 15% to about 40% (w/w) solubilizing agent (e.g., TPGS or TPGS-1000), from about 30% to about 60% (w/w) lipophilic carrier (e.g., fish oil) and from about 1% to about 10% (w/w) viscosity enhancer (e.g., beeswax). In another embodiment, the soft gel capsule of the present application includes omega-3-fatty acids, vitamin C, solubilizing agent (e.g., TPGS or TPGS-1000), beeswax and a lipophilic carrier (e.g., fish oil) enriched with omega-fatty acids. In another embodiment, the omega-fatty acids are combined with a solubilizing agent useful to improve the bioavailability of the omega-fatty acids. Such formulations may further contain additional active ingredients and/or pharmaceutically or cosmetically acceptable additives or vehicles, including solvents, adjuvants, excipients, sweeteners, fillers, colorants, flavoring agents, lubricants, binders, moisturizing agents, preservatives and mixtures thereof. The formulations may be suitable for topical (e.g., a cream, lotion, gel, ointment, dermal adhesive patch), oral (e.g., a soft gel, capsule, tablet, caplet, granulate), or parenteral (e.g., suppository, sterile solution) administration. Among the acceptable vehicles and solvents that may be employed for administration by injection are water, mildly acidified water (e.g. acidified carbonated water), Ringer's solution and isotonic sodium chloride solution. In some embodiments, the formulation is in the form of a drinkable liquid or syrup and can be formulated in a mildly acidified water (e.g. acidified carbonated water) as the carrier. Omega-3-fatty acids, when combined with a solubilizing agent of the present application, can be administered to a warm-blooded animal, particularly a human, in need of the prophylaxis or therapy. The method comprises administering to such human or warm-blooded animal, an effective amount of a water-soluble formulation of the present application. When the hydrophobic moiety of the solubilizing agent is linked to the hydrophilic moiety through a linker, which is cleavable in vivo, the formulation can provide an additional benefit for the patient. In vivo, the solubilizing agent is hydrolyzed by enzymes and is systemically converted back to the respective tocopherol with concomitant release of the omega-3-fatty acids.

The pharmaceutical composition can be prepared according to known methods. Formulations are described in detail in a number of sources, which are well known and readily available to those skilled in the art. For example, Remington's Pharmaceutical Science by E. W. Martin describes formulation, which can be used in connection with the subject present application. In general, the compositions of the subject present application are formulated such that an effective amount of the lipophilic bioactive molecule is provided in the composition. In accordance with the present application, pharmaceutical compositions are provided which comprise, an active ingredient as described, supra, and an effective amount of one or more pharmaceutically acceptable excipients, vehicles, carriers or diluents. Examples of such carriers include ethanol, dimethyl sulfoxide, glycerol, silica, alumina, starch, and equivalent carriers and diluents. Further, acceptable carriers can be either solid or liquid. Solid form preparations include powders, tablets, pills, capsules, cachets, suppositories and dispersible granules. A solid carrier can be one or more substances, which may act as diluents, flavoring agents, solubilizing agents, lubricants, suspending agents, binders, preservatives, tablet disintegrating agents or encapsulating materials.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration, the compositions can take the form of tablets or lozenges formulated in conventional manner.

The disclosed pharmaceutical compositions can be subdivided into unit doses containing appropriate quantities of the active component. The unit dosage form can be a packaged preparation, such as packeted tablets, capsules, and powders in paper or plastic containers or in vials or ampoules. Also, the unit dosage can be a liquid based preparation or formulated to be incorporated into solid food products, chewing gum, or lozenges. Pharmaceutically acceptable salts (counter ions) can be conveniently prepared by ion-exchange chromatography or other methods as are well known in the art. The formulations of the present application can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the present application, such as water, ethanol, propylene glycol, mineral oil, vegetable oil and dimethylsulfoxide (DMSO).

The compositions of the present application may be administered orally, topically, parenterally or rectally in dosage unit formulations containing conventional non-toxic pharmaceutically acceptable carriers, adjuvants and vehicles. It is further understood that the best method of administration may be a combination of methods. The term parenteral as used herein includes subcutaneous injections, intradermal, intravascular (e.g., intravenous), intramuscular, spinal, intrathecal injection or like injection or infusion techniques. The formulations are in a form suitable for oral use, for example, as tablets, troches, lozenges, aqueous or oily suspensions, dispersible powders or granules, emulsion, hard or soft capsules, soft gel capsules, or syrups or elixirs. The formulations described herein may be prepared according to any method known in the art for the manufacture of pharmaceutical formulations and nutraceuticals, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid. Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

In one embodiment, the formulations of the present application may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents. Syrups and elixirs may be formulated with sweetening agents, for example glycerol, propylene glycol, sorbitol or sucrose. Such formulations may also contain a demulcent, a preservative, and flavoring and coloring agents. The formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

For administration to non-human animals, the formulations of the present application may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also be added as a food or drink supplement for humans. Dosage levels (with respect to lipophilic bioactive molecule) of the order of from about 1 mg to about 250 mg per kilogram of body weight per day are useful. For example, a dosage level from about 25 mg to about 150 mg per kilogram of body weight per day, are useful. The amount of active ingredient that may be combined with the carrier materials to produce a single dosage form will vary depending upon the condition being treated and the particular mode of administration. Dosage unit forms will generally contain between from about 1 mg to about 500 mg of the lipophilic bioactive molecule (e.g., omega-fatty acids, omega-3-fatty acids (e.g., ALA, DHA) and carotenoids (e.g., astaxanthin, fucoxanthin, cantaxanthin and the like). For example, dosage unit forms of about 1 mg to about 250 mg, about 1 mg to about 100 mg or 1 mg to about 80, 60, 40, 20 or 10 mg are useful. Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy. The present application also provides packaged formulations and instructions for use of the tablet, capsule, soft gel capsule, elixir, etc. Typically, the packaged formulation, in whatever form, is administered to an individual in need thereof that requires an increase in the amount of omega-3-fatty acids in the individual's diet. Typically, the dosage requirement is between about 1 to about 4 dosages a day.

Exemplary Formulations Including Stabilizers:

In another embodiment, the present application provides a formulation which comprises: (a) an omega-fatty acids; (b) a solubilizing agent (e.g TPGS etc . . . ); (c) a water-soluble reducing agent (stabilizer) (e.g., vitamin C, a vitamin C derivative or mixtures thereof); (d) EDTA; and (e) sodium bisulfite. In another embodiment, the ratio of the omega-fatty acids to said solubilizing agent is from about 1:0.3 (w/w) to about 1:20 (w/w), from about 1:1 (w/w) to about 1:20 (w/w), from about 1:1 (w/w) to about 1:10 (w/w), from about 1:1.3 (w/w) to about 1:5 (w/w), from about 1:2 (w/w) to about 1:4 (w/w), about 1:3 (w/w); from about 1:0.3 (w/w) to about 1:1 (w/w), or from about 1:0.5 (w/w) to about 1:2 (w/w). In another embodiment, the ratio of the omega-fatty acids to the TPGS is from about 1:2 to about 1:4, or about 1:3. In another embodiment, the ratio of the omega-fatty acids to the TPGS is from about 1:2 to about 1:4, or about 1:3.

In another embodiment, the present application provides a formulation which comprises: (a) an omega-fatty acids; (b) a solubilizing agent (e.g., TPGS or PTGS-1000); (c) vitamin C, a vitamin C derivative, or combinations thereof; (d) EDTA, and (e) sodium bisulfite. In one embodiment, the omega-fatty acids is present in the formulation in an amount of at least about 0.5% by weight, at least about 1% by weight, at least about 1.5% by weight, at least about 2% by weight, at least about 2.5% by weight, at least about 3% by weight, at least about 3.5% by weight, at least about 4% by weight, at least about 4.5% by weight or at least about 5% by weight. In another embodiment, the omega-fatty acids is present in the formulation in an amount of at least about 95% by weight, at least about 96% by weight or at least about 97% by weight.

In another embodiment, the present application provides a formulation which comprises: (a) alpha-linolenic acid; (b) a solubilizing agent (e.g., TPGS or TPGS-1000); (c) a stabilizer; (d) EDTA, and (e) sodium bisulfite. In another embodiment, the present application provides a formulation which comprises: (a) alpha-linolenic acid; (b) a solubilizing agent; (c) Vitamin C, a Vitamin C derivative, or combinations thereof; (d) EDTA, and (e) sodium bisulfite. In another embodiment, the present application provides a formulation which comprises: (a) alpha-linolenic acid; (b) TPGS or TPGS-1000; (c) Vitamin C, a Vitamin C derivative, or combinations thereof; (d) EDTA, and (e) sodium bisulfite. In another embodiment, the present application provides a formulation which comprises: (a) linoleic acid; (b) a solubilizing agent (e.g., TPGS or TPGS-1000); (c) a stabilizer; (d) EDTA, and (e) sodium bisulfite. In another embodiment, the present application provides a formulation which comprises: (a) linoleic acid; (b) a solubilizing agent; (c) Vitamin C, a Vitamin C derivative, or combinations thereof. As provided throughout the present application, unless specified otherwise, the use of the solubilizing agent, even when exemplified by the phrase "e.g., TWEEN-85, TPGS or TPGS-1000" for example, may include each of the disclosed solubilizing agents individually, and their mixtures thereof.

In one embodiment, the present application provides a formulation which comprises: (a) oleic acid; (b) a solubilizing agent; (c) a stabilizer; (d) EDTA, and (e) sodium bisulfite. In another embodiment, the present application provides a formulation which comprises: (a) oleic acid; (b) a solubilizing agent; and (c) Vitamin C, a Vitamin C derivative, or combinations thereof; (d) EDTA, and (e) sodium bisulfite. In another embodiment, the present application provides a formulation which comprises: (a) oleic acid; (b) TPGS or TPGS-1000; and (c) Vitamin C, a Vitamin C derivative, or combinations thereof; (d) EDTA, and (e) sodium bisulfite. In another embodiment, the formulation comprises: (a) gamma linolenic acid; (b) a solubilizing agent; (c) a stabilizer; (d) EDTA, and (e) sodium bisulfite. In another embodiment, the formulation comprises: (a) gamma linolenic acid; (b) a solubilizing agent; (c) Vitamin C, a Vitamin C derivative, or combinations thereof; (d) EDTA, and (e) sodium bisulfite. In another embodiment, the formulation comprises: (a) gamma linolenic acid; (b) TPGS-1000; (c) Vitamin C, a Vitamin C derivative, or combinations thereof; (d) EDTA, and (e) sodium bisulfite. In another embodiment, the formulation comprises: (a) docosahexaenoic acid; (b) a solubilizing agent (e.g., TPGS or TPGS-1000); (c) a stabilizer; (d) EDTA, and (e) sodium bisulfite. In another embodiment, the formulation comprises: (a) docosahexaenoic acid; (b) a solubilizing agent; (c) Vitamin C, a Vitamin C derivative, or combinations thereof; (d) EDTA, and (e) sodium bisulfite. In another embodiment, the formulation comprises: (a) docosahexaenoic acid; (b) TPGS or TPGS-1000; (c) Vitamin C, a Vitamin C derivative, or combinations thereof; (d) EDTA, and (e) sodium bisulfite. In one embodiment, the formulation includes from about 0.01% (w/w) to about 5% (w/w) of docosahexaenoic acid. In another embodiment, the formulation includes from about 0.01% (w/w) to about 0.1% (w/w) of docosahexaenoic acid. In another embodiment, the formulation includes from about 0.01% (w/w) to about 1% (w/w) of docosahexaenoic acid. In another embodiment, the formulation includes from about 0.1% (w/w) to about 1% (w/w) of docosahexaenoic acid. In another embodiment, the formulation includes from about 0.1% (w/w) to about 0.75% (w/w) of docosahexaenoic acid. In another embodiment, the formulation includes from about 1% (w/w) to about 3% (w/w) of docosahexaenoic acid. In another embodiment, the formulation includes from about 0.05% (w/w) to about 0.25% (w/w) of docosahexaenoic acid. In another embodiment, the formulation comprises: (a) eicosapentaenoic acid; (b) a solubilizing agent (e.g., TWEEN-85, TPGS or TPGS-1000); (c) a stabilizer; (d) EDTA, and (e) sodium bisulfite. In another embodiment, the formulation comprises: (a) eicosapentaenoic acid; (b) a solubilizing agent; (c) Vitamin C, a Vitamin C derivative, or combinations thereof; (d) EDTA, and (e) sodium bisulfite. In another embodiment, the formulation comprises: (a) eicosapentaenoic acid; (b) TWEEN-85, TPGS or TPGS-1000; (c) Vitamin C, a Vitamin C derivative, or combinations thereof; (d) EDTA, and (e) sodium bisulfite. In another embodiment, the formulation comprises from about 0.01% (w/w) to about 5% (w/w) of eicosapentaenoic acid; about 0.01% (w/w) to about 0.1% (w/w); about 0.01% (w/w) to about 1% (w/w); about 0.1% (w/w) to about 1% (w/w); about 0.1% (w/w) to about 0.75% (w/w); 1% (w/w) to about 3% (w/w); and about 0.05% (w/w) to about 0.25% (w/w) of eicosapentaenoic acid.

Methods:

Methods of Making the Formulations:

The present application also provides methods (e.g., processes) of making the formulations and compositions of the present application. In one embodiment, the lipophilic bioactive molecule (e.g., omega-3-fatty acids), solubilizing agent and reducing agent (e.g., vitamin C or a water-soluble vitamin C derivative), EDTA, and sodium bisulfite, and optionally other components of the formulation are placed in a container. A solvent is then added and the mixture is optionally heated, thereby dissolving the components and forming the formulation. In another exemplary embodiment, the lipophilic bioactive molecule (e.g., omega-3-fatty acids) is dissolved in a solvent optionally using heat. The solubilizing agent, the reducing agent (e.g., vitamin C or a water-soluble vitamin C derivative), EDTA, and sodium bisulfite and optionally other components are added to the above solution creating a mixture, which is stirred and optionally heated to dissolve all components in the mixture, thus creating the formulation. In another embodiment, a solubilizing agent is dissolved in a solvent (e.g., water). The lipophilic bioactive molecule (e.g., omega-3-fatty acids), the reducing agent (e.g., vitamin C or a water-soluble vitamin C derivative), EDTA, and sodium bisulfite, together with any optional components are added and dissolved in the above solution (optionally using heat), thus creating the formulation. In another exemplary embodiment, the reducing agent (e.g., vitamin C or a water-soluble vitamin C derivative) is dissolved in a solvent of choice. The omega-3-fatty acids and the solubilizing agent, EDTA, and sodium bisulfite together with any optional components are added and are dissolved in the solution (optionally using heat), thus creating the formulation.

Exemplary Processes:

In a particular example, the solubilizing agent is as disclosed herein. In one embodiment, the solubilizing agent used in the methods of the present application is TWEEN-85, TPGS or TPGS-1000. In one example, the omega-fatty acid is solubilized in the above emulsion in the form of micelles that are formed between the omega-fatty acids and the solubilizing agent. In one example, the micelles have a median particle size of less than about 60 nm (e.g., between about 10 and about 30 nm). In one example, the present application provides an omega-3-fatty acids stock solution, which is prepared by a method according to any of the above embodiments. In one example, the above water-soluble omega-3-fatty acids stock solution can be used to prepare a beverage of the present application. In one embodiment, the above method further includes contacting the water-soluble omega-fatty acids stock solution with an original beverage to form an omega-fatty acids beverage of the present application. Exemplary original beverages useful in the methods of the present application are disclosed herein. Exemplary lipophilic bioactive molecules, which can be stabilized using any of the above methods include omega-3-fatty acids (e.g., docosahexaenoic acid (DHA), eicosapentaenoic acid (EPA) and alpha-linolenic acid (ALA)), omega-6-fatty acid, omega-9-fatty acid, essential oils, flavor oils and lipophilic vitamins.

In one example, the amount of water-soluble reducing agent that is contacted with the above emulsion is equivalent to an over-stoichiometric mole ratio with respect to the omega-fatty acids. In another example, the amount is equivalent to a ratio of omega-fatty acids to water-soluble reducing agent of about 1:1 to about 1:10 (w/w); about 1:1 to about 1:8 (w/w), about 1:1 to about 1:6 (w/w) or about 1:1 to about 1:4 (w/w), or about 1:1 to about 1:3 (w/w).

Additives or Carriers for Stabilized Surfactants and Omega-3 Ethyl Ester Emulsions:

The pre-drying emulsion (or emulsion) of the present application may include about 0.1% by weight to about 99% by weight additive or carrier, wherein the additive or carrier may also include a sweetener, a flavoring agent, a coloring agent, an anti-foaming agent, a nutrient, calcium or a calcium derivative, an energy-generating additive, an herbal supplement, a concentrated plant extract, a preservative, and/or combinations thereof.

In one aspect, the additive or carrier may include a gum and maltodextrin. In another aspect, the additive may be selected from the group consisting of crystalline cellulose, α-cellulose cross-linked carboxymethyl cellulose sodium, cross-linked starch, gelatin, casein, gum tragacanth, polyvinylpyrrolidone, chitin, chitosan, dextrin, kaolin, silicon dioxide hydrate, colloidal silicon dioxide, light silica, synthetic aluminum silicate, synthetic hydrotalcite, titanium oxide, dry aluminum hydroxy gel, magnesium carbonate, calcium carbonate, precipitated calcium carbonate, bentonite, aluminum magnesium metasilicate, calcium lactate, calcium stearate, calcium hydrogen phosphate, phosphoric acid anhydride, calcium hydrogen and talc. In one aspect, the additive comprises flowing agents selected from silicon dioxide and titanium oxide that promotes flowability or powdery characteristics of the dry powder. In one aspect, the emulsion comprises one or more additives selected from the group consisting of crystalline cellulose, α-cellulose, cross-linked carboxymethyl cellulose sodium, cross-linked starch, gelatin, casein, gum tragacanth, chitin, chitosan, calcium hydrogen phosphate, calcium hydrogen and precipitated calcium carbonate, and combinations thereof. In another aspect, the additive is comprised of wetting agents to assist in the dissolution of the dry powder, when the dry powder is dissolved in water. Such agents may include lecithin and the like.

In another aspect, the additives may include polymers that are added in an amount such that, where desired, the solution resulting from the re-dissolved powder of the present application remains substantially clear. The additive may include cellulosic polymers. Exemplary cellulosic polymers that may be used include hydroxypropyl methyl cellulose acetate, hydroxypropyl methyl cellulose, hydroxypropyl cellulose, methyl cellulose, hydroxyethyl methyl cellulose, hydroxyethyl cellulose acetate and hydroxyethyl ethyl cellulose. In another aspect, the polymers may include hydroxypropyl methyl cellulose and hydroxypropyl cellulose acetate. In another aspect, the polymers contain at least one ionizable substituent, which may be either ether-linked or ester-linked. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, etc.

In another aspect, exemplary cellulosic polymers may include hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, carboxymethyl ethyl cellulose, ethyl carboxymethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate. In another aspect, the cellulosic polymers may contain a non-aromatic carboxylate group, such as hydroxypropyl methyl cellulose acetate succinate, hydroxypropyl methyl cellulose succinate, hydroxypropyl cellulose acetate succinate, hydroxyethyl methyl cellulose acetate succinate, hydroxyethyl methyl cellulose succinate, hydroxyethyl cellulose acetate succinate and carboxymethyl ethyl cellulose.

Where it is desired to provide coloring pigments to the formulation (emulsions, powders and solutions), various pigments may be added to the formulation. Examples of such pigments include anthocyanin pigments such as hibiscus pigment, red cabbage pigment, sweet potato pigment and blueberry pigment; flavonoid pigments such as safflower pigment; carotenoid pigments such as potato pigment, dunaliella pigment, carrot pigment, and pigments derived from palm; chlorella pigment; turmeric pigment; naphthoquinone pigment, and the like.

In one embodiment, flavor and/or fragrance ingredients or additives may be added to the formulation. As used herein, the terms "flavor and/or "fragrance ingredient or additives" refer to a variety of flavor and fragrance materials of both natural and synthetic origin. Such materials may include single compounds and mixtures of compounds. Specific examples of such additives may be found in, e.g., in Fenaroli's Handbook of Flavor Ingredients, 1975, CRC Press; Synthetic Food Adjuncts, 1947 by M. B. Jacobs, edited by Van Nostrand; or Perfume and Flavor Chemicals by S. Arctander 1969, Montclair, N.J. (USA). These materials and substances are well known to one of skill in the art of perfuming, flavoring, and/or aromatizing consumer products to imparting an odor and/or a flavor or taste to a product, or to modify the odor and/or taste of the product.

Examples of the perfumes mentioned above include peppermint oil, beefsteak plant oil, spearmint oil, lavender oil, rosemary oil, cumin oil, clove oil, eucalyptus oil, lemon oil, orange oil, lime oil, rose oil, cinnamon oil, pepper oil, vanilla, ginger oil, and the like. Examples of the spices mentioned above include spices extracted from capsicum, cardamon, mints, peppers, turmeric, cumin, sage, parsley, oregano, saffron, rosemary, thyme, and the like.

In one embodiment, the composition further comprises an additive such as a sugar or sugar derivative, such as sucrose, glucose, lactose, levulose, fructose, maltose, ribose, dextrose, isomalt, sorbitol, mannitol, xylitol, lactitol, maltitol, pentatol, arabinose, pentose, xylose and galactose, and combinations thereof. Typically, the compositions of the present application may comprise from 0.01 to 10% by weight, about 10% to 25% by weight, or about 25% to 50% by weight of the above additive, relative to the weight of the dried powder formulation.

In one embodiment, the additives including coloring pigments, perfumes, flavoring and spices may be used in the appropriate concentration to obtain the desired color, flavors, aroma, taste and ultimate clarity of solution.

Drying of Stabilized Surfactants and Omega-3 Ethyl Ester Emulsions:

One aspect of the drying method for the stabilized emulsion includes a spray drying method. The spray-drying method may include, for example, a method for spraying from a high-pressure nozzle. In another aspect, the method for spray-drying uses a centrifugal force, such as an atomizer. The gas or air that may be used for the spray drying includes heated air or hot air at a temperature sufficient to dry the powder having the desired moisture content. In one aspect, the gas is an inert gas such as nitrogen or nitrogen-enriched air.

In one aspect, the hot gas temperature may be at about 50° C. to 300° C., from about 60° C. to 100° C., from about 60° C. to 250° C., from about 75° C. to about 185° C., from about 100° C. to about 180° C., about 180° C. to about 190° C., or about 180° C. The high pressure that may be used for the spray during process used in a high pressure nozzle may include about 10 to 1,000 psi, about 100 to about 800 psi, about 200 to about 500 psi. The spray drying may be carried out under conditions such that the residual water or residual moisture content of the dry powder may be controlled to about 1% to about 6%, about 1% to about 5%, about 2% to about 6%, about 3% to about 6%, about 3% to about 5%. According to the present method, without being bound by any particular theory presented herein, it was determined that lower moisture content or higher moisture content than the desired ranges using the present methods as described herein, results in a powder composition that may lose its ability to re-dissolve in water, resulting in solutions that are cloudy and not clear. On the other hand, it was determined that higher residual moisture of the dry powder than the above ranges obtained by the present methods provides powder formulations that may coagulate.

In one aspect, the emulsions may then be sprayed dried in conventional spray drying equipment from commercial suppliers, such as Buchi, Niro, Yamato Chemical Co., Okawara Kakoki Co., and similar commercially available spray drier. Spray drying processes, such as rotary atomization, pressure atomization and two-fluid atomization may also be used. Examples of the devices used in these processes include Parubisu Mini-Spray GA-32 and Parubisu Spray Drier DL-41 (Yamato Chemical Co.) or Spray Drier CL-8, Spray Drier L-8, Spray Drier FL-12, Spray Drier FL-16 or Spray Drier FL-20, (Okawara Kakoki Co.), may be used for the spray drying method using rotary-disk atomizer. The nozzle of the atomizer that produces the powder of the present application may include, for example, nozzle types 1A, 1, 2A, 2, 3 (Yamato Chemical Co.) or similar commercially available nozzles, may be used for the above-mentioned spray drier. In addition, disks type MC-50, MC-65 or MC-85 (Okawara Kakoki Co.) may be used as rotary disks of the spray-drier atomizer.

In one aspect, the spray drying devices traditionally used for the industrial manufacture of a milk or coffee powder may also be employed in the present method. See Jensen J. D., Food Technology, June, 60-71, 1975. In one aspect, the spray drying devices may include those described in U.S. Pat. No. 4,702,799 (Nestle). In one embodiment, operation of the spray drier may be performed at about 200-400° C. at the end of the spray nozzle where the rest of the device may be operated at a lower temperature which may reach the air outlet temperature, such as the sprayer described in U.S. Pat. No. 3,065,076 (Nestle).

In another aspect, the spray-drying apparatus used in the process of the present application may be any of the various commercially available apparati. Representative examples of spray drying apparati are the Anhydro Dryers (Anhydro Corp., Attleboro Falls, Mass.), the Niro Dryer (Niro Atomizer Ltd., Copenhagen, Denmark) or a Leaflash apparatus (CCM Sulzer). In one aspect, a spray-drier with a pressure nozzle may be used.

In another aspect, the powder obtained from the drying process may comprise 10% by weight, 20% by weight, 30% by weight, 40% by weight, 50% by weight, 60% by weight, 70% by weight, 80% by weight, or 90% by weight or more of particles having an average particle size in the range from about 5 to 1,000 microns, from about 10 to 500 microns, from about 10 to 350 microns, from about 20 to 250 microns, or about 40 to 200 microns, or about 50 to 150 microns. In one aspect, the powder obtained from the drying process may comprise of about 20% to 80% by weight of particles having an average particle size of about 50 to 150 microns.

The dry composition of the present application may be formulated to provide a dry powder that is stable, and may form a partially turbid solution, a milky or cloudy solution, or a clear solution as desired. Where a substantially clear solution or composition is not desired, such as a milky or cloudy solution or composition is desired as obtained from the dry powder, the ratio of the solubilizing agent, such as TPGS, to the omega fatty acid may be reduced. For example, the ratio (wt/wt) of TPGS to omega fatty acid (TPGS:Omega fatty acid) may be reduced to a range of about 2:1 to about 1.5:1, about 1.3:1, about 1:1, or 0.9:1 or less.

The dry powder formulation of the present application provides omega fatty acids that are stable to decomposition. Without being bound by any theory presented herein, it is believed that the judicious selection of the solid support allows the encapsulation of the omega fatty acids, provides substantially no surface oil and shields the omega fatty acids from oxidation by exposure to ambient air. In addition, the dry powder formulation is readily re-dissolved in water and forms a clear solution.

The concentrated powder may be prepared as dry preparations, such as, for example, a powder, a granular material, a crystalline material, other types of dry particle preparations or combinations thereof. In one aspect, the dry preparations may be prepared by mixing the ingredients and compositions, as disclosed herein, to form a concentrated solution, and then drying the solution to a dry powder form by conventional drying methods. Representative drying methods may include, for example, lyophilization (or freeze drying), spray drying, fluid bed drying, drum drying, pulse combustion drying and various combinations thereof. In one aspect of the drying method, the method is a spray drying method.

Surfactants or Solubilizing Agents:

One or more surfactants (or solubilizing agents), or a mixture of surfactants may be used in the present formulations. Representative surfactants employed may include: HLB≥10 surfactants such as Poloxamer 188, Polysorbate 80, Polysorbate 20, Vit E-TPGS, Solutol HS 15, PEG-40 Hydrogenated castor oil (Cremophor RH40), PEG-35 Castor oil (Cremophor EL), PEG-8-glyceryl capylate/caprate (Labrasol), PEG-32-glyceryl laurate (Gelucire 44/14), PEG-32-glyceryl palmitostearate (Gelucire 50/13); HLB 8-12 such as Polysorbate 85, Polyglyceryl-6-dioleate (Caprol MPGO), Mixtures of high and low HLB emulsifiers; and LB≤8 such as Sorbitan monooleate (Span 80), Capmul MCM, Maisine 35-1, Glyceryl monooleate, Glyceryl monolinoleate, PEG-6-glyceryl oleate (Labrafil M 1944 CS), PEG-6-glyceryl linoleate (Labrafil M 2125 CS), Oleic acid, Linoleic acid, Propylene glycol monocaprylate (e.g. Capmul PG-8 or Capryol 90), Propylene glycol monolaurate (e.g., Capmul PG-12 or Lauroglycol 90), Polyglyceryl-3 dioleate (Plurol Oleique CC497), Polyglyceryl-3 diisostearate (Plurol Diisostearique) and Lecithin with and without bile salts.

Batch Process for Preparing Stabilized TPGS and Omega-3 Ethyl Ester Composition:

Generally, the process for preparing stabilized TPGS/Omega-3 ethyl esters compositions may include heating the TPGS at an elevated temperature sufficient to melt the TPGS. The mixture may be performed in an inert atmosphere, such as under nitrogen. A mixture of water, di-sodium EDTA or calcium disodium EDTA, ascorbic acid, vitamin C palmitate and sodium bisulfite is added to the TPGS. In one embodiment, the water is heated to about 50° C. before the addition of di-sodium EDTA or calcium disodium EDTA, ascorbic acid, vitamin C palmitate, sodium bisulfite and an antioxidant such as alpha tocopherol or mixture of alpha, beta, gamma and delta forms of tocopherols, or a blend of a mixture of tocopherols that is high in delta tocopherol, Fortium MTD10 (MTD10, Kemin Food Technologies), or a water insoluble antioxidants, may be heated to above 45° C., or about 45° C. to 55° C. and then added to the combined mixture.

In another embodiment, a vessel containing water is heated to about 50° C., and a mixture of di-sodium EDTA or calcium disodium EDTA, ascorbic acid, vitamin C palmitate and sodium bisulfite is added to the vessel and heated to about 45° C. to about 55° C. In certain aspects of the process, sodium metabisulfite, potassium bisulfite, or potassium metabisulfite may be used in place of sodium bisulfite. Fortium MTD10 is preheated above 45° C., or about 45° C. to 55° C. and then added to the combined mixture. TPGS may be pre-heated to about 45° C. to about 55° C. and then added to a vessel.

The resulting mixture, prepared in the embodiment described above, may be heated and stirred at an elevated temperature for a sufficient period of time to allow complete mixing. The mixture may be heated at about 45° C. to about 98° C., or about 55° C. to 98° C., about 85° C. to 98° C., about 90° C. to 98° C., or about 95° C. to 97° C. In one embodiment, the mixture is heat above 95° C. for a sufficient period of time to provide a homogeneous slurry. At the present state of the composition that is described as a "homogeneous slurry" (or solution) means that the slurry composition comprising the various elements or additives are sufficiently well mixed. In a particular aspect of the homogeneous slurry at the present state, the slurry has the appearance of thick, white or off white cottage cheese-like material. Depending on the batch size, the heated mixture may be heated at the desired temperature for at least 10 minutes, at least 15 minutes, at least 30 minutes, at least 45 minutes or at least about 60 minutes to attain a homogeneous solution. Homogeneity of the slurry may be determined by sampling of the mixture, cooling the sample to about 25° C. and determining whether the solution remains substantially homogeneous. The resulting stirred slurry is cooled at a rate of about 5° C. to 20° C. per hour, 5° C. to 15° C. per hour, or about 10° C. per hour until the mixture reaches about 25° C. or at ambient temperature. The resulting homogeneous solution is transferred to storage container or vessel under nitrogen. The solution may be stored in the storage container or prepared for bottling in the desired bottling containers.

As described herein, the methods may be used for batch processing to prepare the composition. However, continuous processing of the described methods may also be employed.

A.1. Into a 500 liters vessel was added purified water (119.3 kg). The vessel was heated to about 50° C. under nitrogen, and the solution was agitated for about 5 minutes. To the vessel was added Di-Na EDTA (2.045 kg), ascorbic acid (3.408 kg), vitamin C palmitate (ascorbyl palmitate, 2.556 kg) and sodium bisulfite (0.733 kg). Fortium MTD10 (2.556 kg) was preheated in a separate vessel to about 45-55° C., and added to the 500 liters vessel. The resulting vessel was stirred and heated to about 95-97° C. for about 15 minutes. TPGS (34.08 kg) was preheated in a separate vessel to 45-55° C., and added to the 500 liters vessel. The resulting mixture was stirred for about 15 minutes until the solution is homogeneous. Omega-3 ethyl esters (17.04 kg) was added to the vessel, and the mixture was heated to about 95-97° C. for about 30 minutes. A 4 oz sample was obtained, allowed to cool to about 25° C. and tested for solution homogeneity. The mixture in the vessel was stirred until the solution is homogeneous.

As provided herein, the omega-3 ethyl esters that are typically employed may have a purity range of about 70-85%, 80-85% and 85-90%. However, higher purity or lower purity ranges may also be employed.

The resulting stirred mixture was cooled at a rate of about 10° C. per hour until the mixture was cooled to about 25° C. The solution was stirred at 25° C. for 5 minutes. The resulting solution was transferred and stored in a shipping container under nitrogen. In one embodiment, the aqueous solution is prepared under conditions that are suited for human consumption and is further treated for the inactivation of microbes by a process selected from the group consisting of pasteurization, aseptic packaging, membrane permeation, sonication or combinations thereof.

"O3-EE" as used herein, refers to omega-3 ethyl ester. Similarly, "Ethyl ester(s)" as used herein, refers to omega-3 ethyl ester.

A.1.3. Into a 500 liters vessel was added purified water (119.3 kg). The vessel was heated to about 50° C. under nitrogen, and the solution was agitated for about 5 minutes. To the vessel was added calcium disodium EDTA (2.045 kg), ascorbic acid (3.408 kg), vitamin C palmitate (ascorbyl palmitate, 2.556 kg) and sodium bisulfite (0.0733 kg). Fortium MTD10 (2.556 kg) was preheated in a separate vessel to about 45-55° C., and added to the 500 liters vessel. The resulting vessel was stirred and heated to about 95-97° C. for about 15 minutes. TPGS (34.08 kg) was preheated in a separate vessel to 45-55° C., and added to the 500 liters vessel. The resulting mixture was stirred for about 15 minutes until the solution is homogeneous. Omega-3 ethyl esters (17.04 kg) was added to the vessel, and the mixture was heated to about 95-97° C. for about 30 minutes. A 4 oz sample was obtained, allowed to cool to about 25° C. and tested for solution homogeneity. The mixture in the vessel was stirred until the cooled solution is substantially clear.

The resulting stirred mixture was cooled at a rate of about 10° C. per hour until the mixture was cooled to about 25° C. The solution was stirred at 25° C. for 5 minutes. The resulting solution was transferred and stored in a shipping container under nitrogen.

A.2. Into a 22 liter round bottom flask under a blanket of nitrogen was added water (5.910 kg). To the stirred water was added ascorbic acid (0.170 kg), ethylenediaminetetraacetic acid disodium salt dihydrate (Di-Na EDTA, 0.101 kg), Fortium MTD10 (0.127 kg), L-ascorbic acid-6-palmitate (0.127 kg) and sodium bisulfite (0.0036 kg). The resulting mixture was stirred, heated to 90-95° C. for about 55 minutes. TPGS (1.694 kg) was heated to about 50° C. and then added to the mixture. The resulting solution was stirred at 90-95° C. for about 30 minutes. 90% Ethyl Esters (0.844 kg) was added to the flask by cannula under nitrogen pressure, and the resulting mixture was stirred at 96-98° C. for about 30 minutes.

The mixture was cooled from about 97° C. to about 31° C. in about 1 hour. The resulting homogeneous mixture was bottled and stored under nitrogen.

A.1.5 Into a 500 liters vessel was added purified water (119.3 kg). The vessel was heated to about 50° C. under nitrogen, and the solution was agitated for about 5 minutes. To the vessel was added Di-Na EDTA (2.045 kg), ascorbic acid (3.408 kg), vitamin C palmitate (ascorbyl palmitate, 2.556 kg) and sodium bisulfite (0.0733 kg). Alpha-D-tocopherol (2.56 kg) was preheated in a separate vessel to about 45-55° C., and added to the 500 liters vessel. The resulting vessel was stirred and heated to about 95-97° C. for about 15 minutes. TPGS (34.08 kg) was preheated in a separate vessel to 45-55° C., and added to the 500 liters vessel. The resulting mixture was stirred for about 15 minutes until the solution is homogeneous. Omega-3 ethyl esters (17.04 kg) was added to the vessel, and the mixture was heated to about 95-97° C. for about 30 minutes. A 4 oz sample was obtained, allowed to cool to about 25° C. and tested for solution homogeneity. The mixture in the vessel was stirred until the solution is homogeneous.

The resulting stirred mixture was cooled at a rate of about 10° C. per hour until the mixture was cooled to about 25° C. The solution was stirred at 25° C. for 5 minutes. The resulting solution was transferred and stored in a shipping container under nitrogen.

A.3.7 Into a 22 liter round bottom flask under a blanket of nitrogen was added water (5.910 kg). To the stirred water was added ascorbic acid (0.170 kg), ethylenediaminetetraacetic acid calcium disodium salt (Calcium Disodium EDTA, 0.101 kg), Fortium MTD10 (0.127 kg), L-ascorbic acid-6-palmitate (0.127 kg) and sodium bisulfite (0.0036 kg). The resulting mixture was stirred, heated to 90-95° C. for about 55 minutes. TPGS (1.694 kg) was heated to about 50° C. and then added to the mixture. The resulting solution was stirred at 90-95° C. for about 30 minutes. 90% Omega-3 ethyl esters (0.844 kg) was added to the flask by cannula under nitrogen pressure, and the resulting mixture was stirred at 96-98° C. for about 30 minutes.

The mixture was cooled from about 97° C. to about 31° C. in about 1 hour. The resulting homogeneous mixture was bottled and stored under nitrogen.

The aqueous solutions prepared according to the present method provides a clear solution with a clarity range of about 1,000 to 20 NTU, about 100 to 20 NTU or about 20 NTU.

In one embodiment, the clear aqueous solution is prepared under conditions that are suited for human consumption and is further treated for the inactivation of microbes by a process selected from the group consisting of pasteurization, aseptic packaging, membrane permeation, sonication or combinations thereof.

TABLE 1

| Reagents (kg) | A.1.1 | A.1.2 | A.1.3 | A.1.4 | A.2.1 | A.2.2 | A.2.3 | A.2.4 |
|---|---|---|---|---|---|---|---|---|
| Water (purified) | 89.462 | 149.103 | 89.462 | 149.103 | 4.433 | 7.388 | 4.433 | 7.388 |
| Di-Na EDTA | 1.534 | 2.556 | 1.534 | 2.556 | 0.0758 | 0.1263 | 0.0758 | 0.1263 |
| Ascorbic acid | 2.556 | 4.260 | 2.556 | 4.260 | 0.128 | 0.213 | 0.128 | 0.213 |
| Vitamin C palmitate (ascorbyl palmitate) | 1.917 | 3.195 | 1.917 | 3.195 | 0.0953 | 0.159 | 0.0953 | 0.159 |
| Sodium bisulfite | 0.0550 | 0.0916 | 0.550 | | 0.027 | 0.045 | 0.27 | |
| Potassium bisulfite | | | | 0.0916 | | | | 0.045 |
| Fortium MTD10[a] | 1.917 | 3.195 | 1.917 | 3.195 | 0.0953 | 0.159 | 0.0953 | 0.159 |
| TPGS | 25.50 | 42.60 | 25.50 | 42.60 | 1.271 | 2.118 | 1.271 | 2.118 |
| Omega-3 ethyl ester | 10.53 | 17.55 | 10.53 | 17.55 | 0.633 | 1.055 | 0.633 | 1.055 |

[a]In other experiments using the same ratio of reagents and additives, Fortium MTD10 may be replaced with synthetic or natural tocopherol, alpha-D-tocopherol, or a mixture of natural tocopherols.

TABLE 2

| | Experiments Relative Wt/Wt % Ranges of Reagents | | |
|---|---|---|---|
| Reagents | A.3.1 | A.3.2 | A.3.3 |
| 85% Omega-3 ethyl ester | 6.0 to 14 | 5.0 to 15 | 3.0 to 20 |
| TPGS | 13 to 25 | 11 to 27 | 10 to 30 |
| Water | 47 to 88 | 45 to 95 | 40 to 97 |
| Ascorbic acid | 0.01 to 0.5 | 0.001 to 1.0 | 0.001 to 2.0 |
| Disodium EDTA | 0.50 to 2.0 | 0.01 to 2.5 | 0.005 to 5.0 |
| MTD-10 | 0.5 to 3.0 | 0.01 to 5.0 | 0.005 to 10.0 |
| Ascorbic Acid 6-Palmitate | 0.5 to 3.0 | 0.01 to 5.0 | 0.005 to 10.0 |
| Sodium bisulfate | 0.01 to 0.1 | 0.001 to 0.5 | 0.001 to 1.0 |

TABLE 3

| Reagents | Experiments Relative Wt/Wt % Ranges of Reagents | | |
|---|---|---|---|
| | A.3.4 | A.3.5 | A.3.6 |
| 85% Omega-3 ethyl ester | 6.0 to 14 | 5.0 to 15 | 3.0 to 20 |
| TPGS | 13 to 25 | 11 to 27 | 10 to 30 |
| Water | 47 to 88 | 45 to 95 | 40 to 97 |
| Ascorbic acid | 0.01 to 0.5 | 0.001 to 1.0 | 0.001 to 2.0 |
| Calcium Disodium EDTA | 0.50 to 2.0 | 0.01 to 2.5 | 0.005 to 5.0 |
| MTD-10 | 0.5 to 3.0 | 0.01 to 5.0 | 0.005 to 10.0 |
| Ascorbic Acid 6-Palmitate | 0.5 to 3.0 | 0.01 to 5.0 | 0.005 to 10.0 |
| Sodium bisulfate | 0.01 to 0.1 | 0.001 to 0.5 | 0.001 to 1.0 |

Qualitative analysis of the products obtained from the process described herein shows that the product meets all specifications established for fatty acid composition, physical properties, trace impurities and microbials content.

Procedure for Preparing Stabilized Surfactant-Omega-3 Ethyl Ester Emulsions for Spray Drying:

Generally, the process for preparing stabilized TPGS/Omega-3 ethyl esters emulsions include the addition of one or more additives and/or carriers, such as a starch or a polymer, to water, and the resulting mixture is heated above room temperature. The mixture may be heated to about 35° C. to 90° C., about 35° C. to about 80° C., about 35° C. to 75° C., or about 50° C. to 70° C., about 60° C. to 70° C. or about 65° C. Depending on the nature of the additives and the size of the batch, the mixture may be heated from at least about 5 minutes, at least 10 minutes, at least 15 minutes, at least 30 minutes, at least 45 minutes or at least about 60 minutes to about 120 minutes. The resulting mixture is then cooled to below room temperature, about 15° C. to 20° C., about 5° C. to 15° C., or about 10° C. To the stirred mixture is then added TPGS/O3-EE/stabilized composition, and the resulting emulsion is stirred for at least about 5 minutes, about 10 minutes, about 15 minutes, about 30 minutes or at least about 60 minutes to provide the predrying emulsion. The predrying emulsion may be used in the subsequent drying step as disclosed herein.

As provided herein, the additives and/or carriers may include HI-CAP 100 (National Starch), Emcap Starch, TICAMULSION FC (TIC GUMS), Spray gum F (gum acacia with Maltrin-100), natural vanillin, natural maltol, maltodextrin 10-DE, and other additives as disclosed herein and mixtures thereof. In one embodiment, the carrier is maltodextrin and Spray gum F. In one embodiment, the ratio (wt/wt) of water to TPGS/O3-EE/stabilized ranges from about 0.3:1 to 10:1, about 0.5:1 to about 5:1, about 0.5:1 to about 3:1, about 1:1 to about 2.5:1, and about 1.5:1 to about 2:1. In one embodiment, the ratio (wt/wt) of the additives and/or carriers to the TPGS/O3-EE/stabilized composition may range from about 0.1:1 to about 100:1, about 0.1:1 to 50:1; or about 0.3:1 to 30:1, about 0.5:1 to 15:1, or about 0.3:1 to about 10:1.

A.4. Into a vessel equipped with an overhead stirrer as added water (543.5 g), and the water solution was stirred at room temperature. To the vigorously stirred solution was added HI-CAP 100 (National Starch, 108.7 g), and the mixture was stirred for 15 minutes. The resulting mixture was heated to 65.5° C. and mixed for 5 minutes. The mixture was cooled to 10° C. with mixing. TPGS/O3-EE/stabilized emulsion ("OTECH emulsion," 347.8 g) was added and the resulting mixture was stirred for 5 minutes to provide the pre-drying emulsion.

A.5. Into a vessel equipped with an overhead stirrer as added water (1,434 g), and the water solution was stirred at room temperature. To the vigorously stirred solution was added Emcap Starch (Cargill, 648.3 g), and the mixture was stirred for 15 minutes. The resulting mixture was heated to 65.5° C. and mixed for 5 minutes. The mixture was cooled to 10° C. with mixing. TPGS/O3-EE/stabilized emulsion (917.7 g) was added and the resulting mixture was stirred for 5 minutes to provide the pre-drying emulsion.

A.6. Into a vessel equipped with an overhead stirrer as added water (468.7 g), and the water solution was stirred at room temperature. To the vigorously stirred solution was added Emcap Starch (Cargill, 281.3 g), and the mixture was stirred for 15 minutes. The resulting mixture was heated to 65.5° C. and mixed for 5 minutes. The mixture was cooled to 10° C. with mixing. TPGS/O3-EE/stabilized emulsion (250.0 g) was added and the resulting mixture was stirred for 5 minutes to provide the pre-drying emulsion.

A.7. Into a vessel equipped with an overhead stirrer was added water (500 g), and the water solution was stirred at room temperature. To the vigorously stirred solution was added TICAMULSION FC (TIC GUMS, 180.0 g), and the mixture was stirred for 15 minutes. The resulting mixture was heated to 65.5° C. and mixed for 5 minutes. The mixture was cooled to 10° C. with mixing. TPGS/O3-EE/stabilized emulsion (320 g) was added and the resulting mixture was stirred for 5 minutes to provide the pre-drying emulsion.

A.8. Into a vessel equipped with an overhead stirrer was added water (531.9 g), and the water solution was stirred at room temperature. To the vigorously stirred solution was added TICAMULSION FC (TIC GUMS, 255.3 g), and the mixture was stirred for 15 minutes. The resulting mixture was heated to 65.5° C. and mixed for 5 minutes. The mixture was cooled to 10° C. with mixing. TPGS/O3-EE/stabilized emulsion (212.8 g) was added and the resulting mixture was stirred for 5 minutes to provide the pre-drying emulsion.

A.9. Into a vessel equipped with an overhead stirrer was added water (425.0 g), and the water solution was stirred and heated to about 18° C. to 24° C. To the vigorously stirred solution was added Spray gum F (gum acacia with Maltrin-100, 85 g), natural vanillin (0.85 g), natural maltol (0.21 g) and maltodextrin 10-DE (212.5 g), and the mixture was stirred for about 15 minutes. The resulting mixture was heated to about 63° C. to 68° C. and mixed for 5 to 10 minutes. The mixture was cooled to about 7.2° C. to 12.8° C. with mixing. TPGS/O3-EE/stabilized emulsion (425 g) was added and the resulting mixture was stirred for 5 minutes to provide the predrying emulsion.

A.10. Into a vessel equipped with an overhead stirrer was added water (425.0 g), and the water solution was stirred and heated to about 18° C. to 24° C. To the vigorously stirred solution was added Spray gum F (gum acacia with Maltrin-100, 85 g), natural maltol (0.21 g) and maltodextrin 10-DE (212.5 g), and the mixture was stirred for about 15 minutes. The resulting mixture was heated to about 63° C. to 68° C. and mixed for 5 to 10 minutes. The mixture was cooled to about 7.2° C. to 12.8° C. with mixing. TPGS/O3-EE/stabilized emulsion (425 g) was added and the resulting mixture was stirred for 5 minutes to provide the predrying emulsion.

A.11. Into a vessel equipped with an overhead stirrer was added water (425.0 g), and the water solution was stirred and heated to about 18° C. to 24° C. To the vigorously stirred solution was added Spray gum F (gum acacia with Maltrin-100, 85 g), natural vanillin (0.85 g) and maltodextrin 10-DE (212.5 g), and the mixture was stirred for about 15 minutes. The resulting mixture was heated to about 63° C. to 68° C. and mixed for 5 to 10 minutes. The mixture was cooled to about 7.2° C. to 12.8° C. with mixing. TPGS/O3-EE/stabilized emulsion (425 g) was added and the resulting mixture was stirred for 5 minutes to provide the pre-drying emulsion.

A.12. Into a vessel equipped with an overhead stirrer was added water (425.0 g), and the water solution was stirred and heated to about 18° C. to 24° C. To the vigorously stirred solution was added natural vanillin (0.85 g), natural maltol (0.21 g) and maltodextrin 10-DE (297.5 g), and the mixture was stirred for about 15 minutes. The resulting mixture was heated to about 63° C. to 68° C. and mixed for 5 to 10 minutes. The mixture was cooled to about 7.2° C. to 12.8° C. with mixing. TPGS/O3-EE/stabilized emulsion (425 g) was added and the resulting mixture was stirred for 5 minutes to provide the pre-drying emulsion.

be used to solubilize the vitamin (e.g., vitamin E) include TWEEN-85, TPGS, TPGS-1000 and polyoxyethylene sorbitan monooleate, and solubilizing agents as disclosed herein. In another embodiment, the present application provides a beverage produced by any of the above methods of the present application.

In yet another example according to any of the above embodiments, the bioactive, lipophilic molecule is selected from omega-3-fatty acids, omega-6-fatty acid, carotenoids, essential oils, flavor oils and lipophilic vitamins. In one example, the omega-3-fatty acid is a member selected from docosahexaenoic acid (DHA), eicosapentaenoic acid (EPA) and alpha-linolenic acid (ALA).

TABLE 4

| Reagents (grams) | Examples | | | | | | | |
| --- | --- | --- | --- | --- | --- | --- | --- | --- |
| | A.9 | A.9.1 | A.10.1 | A.10.2 | A.11.1 | A.11.2 | A.12.1 | A.12.2 |
| Water | 425 | 575 | 425 | 575 | 425 | 575 | 425 | 575 |
| Spray gum F (gum acacia with Maltrin-100) | 85 | 115 | 85 | 115 | 85 | 115 | | |
| Natural vanillin | 0.85 | 1.15 | | | 0.85 | 1.15 | 0.85 | 1.15 |
| Natural maltol | 0.21 | 0.29 | 0.21 | 0.29 | | | 0.21 | 0.29 |
| Maltodextrin 10-DE | 212.5 | 287.5 | 212.5 | 287.5 | 212.5 | 287.5 | 297.5 | 402.5 |
| TPGS/O3-EE/stabilized | 425 | 575 | 425 | 575 | 425 | 575 | 425 | 575 |

The emulsions prepared according to the above procedure may be dried using various drying methods as provided herein. In one embodiment, the emulsions may be dried using the spray drying methods as described herein. The spray dried composition comprises water content from about 1% to about 10%, from about 1% to about 6%, about 2% to about 5%, about 3% to 4%, about 1% to 3%, about 2% to 3%, about 3% to 6%, about 3% to 5%, or about 3% to 4%. According to the present method, using the compositions described herein, it was determined that lower water content of the dried powder composition provides a cloudy mixture when the powder is re-dissolved in water. Accordingly, the clarity or homogeneity of the aqueous solution containing the compositions as described herein may be controlled by the amount residual water remaining in the dried powders.

Methods of Making the Beverages:

Method for Making an Omega-Fatty Acids Beverage

In another aspect, the present application provides a method for making a beverage (e.g., a non-alcoholic beverage) that includes omega-fatty acids. An exemplary method includes: contacting an original beverage with a water-soluble omega-fatty acids stock solution (e.g., omega-fatty acids-50 stock solution) of the present application. Exemplary original beverages are disclosed herein and include carbonated or uncarbonated water, flavored water, soft drinks, beer and drinkable dairy products. All embodiments described herein above for the method of making a omega-3-fatty acids stock solution equally apply to the method of making a omega-3-fatty acids beverage described in this paragraph. In one example, the method further includes adding a vitamin (e.g., vitamin C, vitamin E, a B-vitamin (e.g., vitamin B-pentapalmitate) or combinations thereof) to the beverage. In one example, when the vitamin (e.g., vitamin E) is added to the beverage, the vitamin is first solubilized in an aqueous medium using a solubilizing agent, such as a solubilizing agent of the present application, and is subsequently added to the beverage. Exemplary solubilizing agents that can The compositions and methods of the present application are further illustrated by the examples that follow. These examples are offered to illustrate, but not to limit the claimed present application.

Methods and Procedures:

As provided herein, the present application provides a method for preparing clear and stable omega-3 fatty acids compositions for use in various food products. In a particular embodiment, the omega-3 fatty acids formulations described herein are nano-emulsions. As disclosed herein, the composition is safe for human consumption. The compositions are ideally GRAS (or ideally FDA-GRAS self-affirmed GRAS (TPGS-1000)), or the composition comprises other food materials. In addition, the composition that are used are inexpensive, readily sourced from bulk materials, and may cost less than about $100/kg.

In one aspect, the ratio of the surfactant to the omega-3 fatty acids is low, such as a ratio of less than 2:1 or about 1:1(w/w). The compositions prepared from the methods described herein are relatively clear at concentration and dilution. The compositions prepared by the present methods provide NTU levels that are in the low double digit numbers, however, in certain formulations, the composition may provide compositions as high as 200 NTU.

In certain embodiments, the formulations comprise a high percentage of the daily allowable dose of the emulsion ingredient such that Omega-3 fatty acids are provided in high delivery dosages. In a particular aspect, the emulsifier that is present does not present a significant taste and odor profile.

Hydrophilic Lipophilic Balance is as defined in the art as HLB=20*Mh/M, where Mh is the molecular mass of the hydrophilic portion of the Molecule, and M is the molecular mass of the whole molecule, giving a result on an arbitrary scale of 0 to 20. An HLB value of 0 corresponds to a completely hydrophobic molecule, and a value of 20 would correspond to a molecule made up completely of hydrophilic components. The HLB value can be used to predict the surfactant properties of a molecule. For example, a value from 0 to 3 indicates an anti-foaming agent; a value from 4 to 6 indicates a W/O (water in oil) emulsifier; a value from 7 to 9 indicates a wetting agent; a value from 8 to 18 indicates an O/W (oil in water) emulsifier; a value from 13 to 15 is typical of detergents; a value of 10 to 18 indicates a solubiliser or hydrotrope. HLB>10 may include Poloxamer 188, Polysorbate 80, Polysorbate 20, Vitamin E-TPGS, Solutol HS 15, PEG-40, Hydrogenated castor oil (Cremophor RH40), PEG-35 Castor oil (Cremophor EL), PEG-8-glyceryl capylate/caprate (Labrasol), PEG-32-glyceryl laurate (Gelucire 44/14), PEG-32-glyceryl palmitostearate (Gelucire 50/13). HLB 8-12 may include Polysorbate 85, polyglyceryl-6-dioleate (Caprol MPGO), TPGS, and/or mixtures of high and low HLB emulsifiers. HLB<8 may include sorbitan monooleate (Span 80), Capmul MCM, maisine 35-1, glyceryl monooleate, glyceryl monolinoleate, PEG-6-glyceryl oleate (Labrafil M 1944 CS), PEG-6-glyceryl linoleate (Labrafil M 2125 CS), oleic acid, linoleic acid, propylene glycol monocaprylate (e.g. Capmul PG-8 or Capryol 90), propylene glycol monolaurate (e.g., Capmul PG-12 or lauroglycol 90), polyglyceryl-3 dioleate (Plurol Oleique CC497), polyglyceryl-3 diisostearate (Plurol Diisostearique) and lecithin with and without bile salts.

The relative solubility of compositions of the present application, including composition comprising, for example, a 2:1 and 1:1 surfactant/omega-3 fatty acids systems in water (or other aqueous solvent system(s)) may be determined by emulsification screening, visual appearance, turbidity, tarticle (emulsion droplet) size by Photon Correlation Spectroscopy (PCS), visual assessment of dilution effects, ambient room temperature (RT) stability at 1, 2 and 4 weeks and established compatibility with beverage matrices. Suitable antioxidants and stabilizers may be added at the desired concentrations to provide the desired compositions.

As provided herein, the compositions of the present application demonstrate significant oxidative stability, and may be tested and determined by storing the composition in vials. The composition may be purged with oxygen and analyzed at various time intervals to determine compositions having the optimal appearance, the assay (by HPLC, for example), by PCS and the physical and chemical stability suitable for use in various food products.

EXAMPLES

Into a 12 Liter round bottomed flask, equipped with a thermometer, an overhead stirrer and a heating mantle, under a blanket of nitrogen gas was added TWEEN-85 (1,600 grams). Ascorbic acid (12.0 grams, 0.07 moles) was added to the flask. Ethylenediaminetetraacetic acid disodium salt dihydrate (35 grams, 0.09 moles) was added to the flask. MTD10 (70 grams) was then added to the flask. L-Ascorbic acid-6-palmitate (70.0 grams, 0.17 moles) was then added to the flask. Water (5,600 grams, 311.1 moles) was then charged to the flask, and the resulting stirred reaction mixture was heated to 90 to 95° C. and maintained at about 90 to 95° C. for two hours.

Denomega D100.3 (300 grams) was charged to the heated flask via cannula under nitrogen, and the resulting mixture was stirred at 90 to 95° C. for 30 minutes. The mixture then turned into an emulsion. The reaction mixture was cooled to about 10-15° C. at a rate of greater than about 10° C. per hour using a temperature controller.

Once the reaction mixture is clear, a sample is obtained from the reaction flask and analyzed. IPC was determined. Solubilization of High Grade EE-Omega's with TPGS:

CAR-T-4: In a microcentrifuge tube, 50% ethyl ester high EPA (70:10)(100 mg, Organic Technologies lot# 09C11498), Vitamin E TPGS (200 mg, Antares lot# TGOC0109002) was combined and heated until a melt was obtained. Then DI water (700 mg) was added and the mixture was heated to 90-100° C. until it became homogeneous. The homogeneous mixture was cooled to room temperature and was slightly opaque. The opaque homogeneous mixture stayed in solution for ~4 days. Then 64.5 mg of the opaque homogeneous mixture was diluted with 30 mL of DI water and the clarity was measured at 7.97 NTU (CAR-T-4-1).

CAR-T-5: In a microcentrifuge tube, 80% ethyl ester high EPA (70:10) (100 mg, Organic Technologies lot# 09C11539), Vitamin E TPGS (200 mg, Antares lot# TGOC0109002) and DI water (700 mg) were combined. The mixture was heated to 90-100° C. until it became homogeneous. The homogeneous mixture was cooled in and ice bath and was opaque. After ~5 days the once opaque homogeneous mixture was observed to be heterogeneous. The mixture was reheated to 90-100° C. until it became homogeneous. The homogeneous mixture was cooled in and ice bath and was an opaque homogeneous mixture. Then 62 mg of the opaque homogeneous mixture was diluted with 30 mL of DI water and the clarity was measured at 14.9 NTU (CAR-T-5-1).

CAR-T-6: In a microcentrifuge tube, 90% ethyl ester high EPA (70:10) (100 mg, Organic Technologies lot# 09C11531), Vitamin E TPGS (200 mg, Antares lot# TGOC0109002) and DI water (700 mg) were combined. The mixture was heated to 90-100° C. until it became homogeneous. After five days the once homogeneous mixture was observed to be heterogeneous. The mixture was reheated to 90-100° C. until it became homogeneous. The homogeneous mixture was cooled in and ice bath and was an opaque homogeneous mixture. Then 60.5 mg of the homogeneous mixture was diluted with 30 mL of DI water and the clarity was measured at 10.2 NTU (CAR-T-6-1).

CAR-T-7: In a microcentrifuge tube, 50% ethyl ester high EPA(70:10)(50 mg, Organic Technologies lot# 09C11498), Vitamin E TPGS (300 mg, Antares lot# TGOC0109002) was combined and heated until a melt was obtained. Then DI water (1050 mg) was added and the mixture was heated to 90-100° C. until it became homogeneous. The homogeneous mixture was cooled in and ice bath and was an opaque homogeneous mixture. Then all of the mixture was diluted with 30 mL of DI water and the clarity was measured at 48.1 NTU.

CAR-T-21: In a 250 mL 3-neck round bottom flask equipped with an overhead stirrer, thermocouple, condenser, heating mantle and a nitrogen inlet, 90% ethyl ester high EPA (70:10)(10.17 g, Organic Technologies lot # 09C11531), Vitamin E TPGS (20 g, Antares lot# TGOC0109002) and DI water (70 g) were combined. The mixture was heated to 95° C. until it became homogeneous, and was held for 30 minutes. Then the homogeneous mixture was cooled in an ice water bath. At 85° C. the opaque homogeneous mixture became a clear homogeneous mixture. After further cooling to 2.8° C., the clarity was measured at 99.2 NTU (CAR-T-21-1). Then 76.2 mg of CAR-T-21-1 was diluted with 30 mL of DI water and the clarity was measured at 3.14 NTU (CAR-T-21-1).

CAR-T-30: In a 250 mL 3-neck round bottom flask equipped with an overhead stirrer, thermocouple, condenser, heating mantle and a nitrogen inlet, Vitamin E TPGS (20.0 g, TR Nutritionals lot #0806001) 90% ethyl ester high EPA (70:10) (10.0 g, Organic technologies lot # 09C11586), and DI water (70.0 g) were combined. The mixture was heated to 95° C. until it became homogeneous, and was held for ~45 minutes. Then the opaque homogeneous mixture was cooled in an ice water bath. After cooling to 5° C., the mixture remained homogeneous but was opaque (CAR-T-30-1). Then 61.1 mg of CAR-T-30-1 was diluted with 30 mL of DI water and the clarity was measured at 72.1 NTU (CAR-T-30-2).

Solubilization of Triglyceride Fish Oils with TPGS:

CAR-T-8: In a microcentrifuge tube, Omega 3 30TG Food Grade Fish Oil (100 mg, Ocean Nutrition Canada Ltd., lot # 21120), Vitamin E TPGS (200 mg, Antares lot# TGOC0109002) and DI water (700 mg) were combined. The mixture was heated to 90-100° C. until it became homogeneous. The homogeneous mixture was cooled to room temperature and was an opaque homogeneous mixture. Then 60 mg of the opaque homogeneous mixture was diluted with 30 mL of DI water and the clarity was measured at 98.6 NTU (CAR-T-8-1). Sample CAR-T-8-1 was then filtered through a 0.2 micron filter and the clarity was measured at 0.682 NTU (CAR-T-8-2).

CAR-T-9: In a microcentrifuge tube, DHA Fish Oil (100 mg, Ocean Nutrition Canada Ltd., lot # 20319), Vitamin E TPGS (200 mg, Antares lot# TGOC0109002) and DI water (700 mg) were combined. The mixture was heated to 90-100° C. until it became homogeneous. The homogeneous mixture was cooled to room temperature and was an opaque homogeneous mixture. Then 70 mg of the opaque homogeneous mixture was diluted with 31 mL of DI water and the clarity was measured at 115 NTU (CAR-T-9-1). Sample CAR-T-9-1 was then filtered through a 0.2 micron filter and the clarity was measured at 0.696 NTU (CAR-T-9-2).

CAR-T-19: In a 250 mL 3-neck round bottom flask equipped with an overhead stirrer, thermocouple, condenser, heating mantle, addition funnel and a nitrogen inlet, Omega 3 30TG Food Grade Fish Oil (11.4 g, Ocean Nutrition Canada Ltd., lot # 21120), Vitamin E TPGS (22.8 g, Antares lot# TGOC0109002) was added and heated to 90° C. until melted. DI Water (70 g, 90° C.) was added via cannula in one portion. After the addition was complete, the mixture was heated to 90° C. until it became homogeneous. The homogeneous mixture (65.6 mg) was diluted with DI water (30 mL) and the clarity was measured at 193 NTU (CAR-T-19-1)

Preparation of the Stabilized Emulsion of Tpgs and High Grade Ee-Oils:

CAR-T-23: In a 250 mL 3-neck round bottom flask equipped with an overhead stirrer, thermocouple, condenser, heating mantle and a nitrogen inlet, Vitamin E TPGS (23.3 g, Antares lot# TGOC0109002), Vitamin C (0.2 g, Sigma lot# 048K1193), EDTA disodium (0.4 g, Sigma lot #078K0085), Vitamin C Palmitate (0.5 g, Alfa Aesar lot # G02P05), Vitamin E (0.5 g, Kemin lot # 0710104918), 90% ethyl ester high EPA(70:10)(11.69 g, Organic Technologies lot # 09C11531) and DI water (82 g) were combined. The mixture was heated to 94° C. until it became homogeneous, and was held for 30 minutes. Then the opaque homogeneous mixture was cooled in an ice water bath. At 73° C. the mixture became clear homogeneous mixture. After further cooling to 23° C., the clarity was measured at 28.1 NTU (CAR-T-23-2). Then 65.3 mg of CAR-T-23-2 was diluted with 30 mL of DI water and the clarity was measured at 2.31 NTU (CAR-T-23-3).

CAR-T-31: In a 250 mL 3-neck round bottom flask equipped with an overhead stirrer, thermocouple, condenser, heating mantle and a nitrogen inlet, Vitamin E TPGS (20.0 g, TR Nutritionals lot #0806001), Vitamin C (0.15 g, Sigma lot# 048K1193), EDTA disodium (0.4 g, Sigma lot #078K0085), Vitamin C Palmitate (0.6 g, Alfa Aesar lot # G02P05), Vitamin E (0.6 g, Kemin lot # 0710104918), 90% ethyl ester high EPA (70:10) (10.0 g, Organic Technologies lot # 09C11586) and DI water (70 g) were combined. The mixture was heated to 95° C. until it became homogeneous, and was held for ~45 minutes. Then the opaque homogeneous mixture was cooled in an ice water bath. After cooling to 5° C., the mixture remained homogeneous but was opaque (CAR-T-31-1). Then 72.4 mg of CAR-T-31-1 was diluted with 30 mL of DI water and the clarity was measured at 87.5 NTU (CAR-T-31-2).

CAR-T-27: In a 250 mL 3-neck round bottom flask equipped with an overhead stirrer, thermocouple, condenser, heating mantle and a nitrogen inlet, Vitamin E TPGS (20.0 g, Antares lot# TGOC0109002), Vitamin C (0.15 g, Sigma lot# 048K1193), EDTA disodium (0.43 g, Sigma lot #078K0085), Vitamin C Palmitate (0.8 g, Alfa Aesar lot # G02P05), Vitamin E (0.8 g, Kemin lot # 0710104918), 90% ethyl ester high EPA(70:10)(10.0 g, Organic technologies lot # 09C11586) and DI water (70 g) were combined. The mixture was heated to 97.7° C. until it became homogeneous, and was held for ~45 minutes. Then the opaque homogeneous mixture was cooled in an ice water bath. At 76° C. the mixture became a clear homogeneous mixture. After further cooling to 22.5° C., the clarity was measured at 67.3 NTU (CAR-T-27-1). Then 70.5 mg of CAR-T-27-1 was diluted with 30 mL of DI water and the clarity was measured at 2.98 NTU (CAR-T-27-2).

Preparation of the Stabilized Emulsion of Tpgs and High Grade Ee-Oils, with Additional Bisulfite:

CAR-T-26: In a 250 mL 3-neck round bottom flask equipped with an overhead stirrer, thermocouple, condenser, heating mantle and a nitrogen inlet, Vitamin E TPGS (20.0 g, Antares lot# TGOC0109002), Vitamin C (0.2 g, Sigma lot# 048K1193), EDTA disodium (0.4 g, Sigma lot #078K0085), Vitamin C Palmitate (0.5 g, Alfa Aesar lot # G02P05), sodium metabisulfite (0.5 g, Sigma-Aldrich lot #01514LH), Vitamin E (0.5 g, Kemin lot # 0710104918), 90% ethyl ester high EPA(70:10)(10.0 g, Organic Technologies lot # 09C11586) and DI water (70 g) were combined. The mixture was heated to 95° C. until it became homogeneous, and was held for 50 minutes. Then the opaque homogeneous mixture was cooled in an ice water bath. At 63° C. the mixture became a clear homogeneous mixture. After further cooling to 22.5° C., the clarity was measured at 48.5 NTU (CAR-T-26-1). Then 66.0 mg of CAR-T-26-1 was diluted with 30 mL of DI water and the clarity was measured at 2.66 NTU (CAR-T-26-2).

CAR-T-25: In a 250 mL 3-neck round bottom flask equipped with an overhead stirrer, thermocouple, condenser, heating mantle and a nitrogen inlet, Vitamin E TPGS (20.0 g, Antares lot# TGOC0109002), Vitamin C (0.2 g, Sigma lot# 048K1193), EDTA disodium (0.4 g, Sigma lot #078K0085), Vitamin C Palmitate (0.5 g, Alfa Aesar lot # G02P05), sodium bisulfite (0.5 g, Sigma lot #06210AE), Vitamin E (0.5 g, Kemin lot # 0710104918), DI water (70 g) and 90% ethyl ester high EPA(70:10)(10.0 g, Organic technologies lot # 09C11531) were combined. The mixture was heated to 92-95° C. until it became homogeneous, and was held for 30 minutes. Then the opaque homogeneous mixture was cooled in an ice water bath. After cooling to 5.4° C., the mixture remained homogeneous and opaque (CAR-T-25-2). Then 60.1 mg of CAR-T-25-2 was diluted with 30 mL of DI water and the clarity was measured at 30.1 NTU (CAR-T-25-1).

Formulation using Ocean Technologies 90% Ethyl Ester (Exp: CAR-T-21):

TPGS-1000 (20 g, Antares), 90% ethyl ester high epa (70:10) (10 g, Organic Technologies) and water (70 g) were charged to a 250 mL 3-neck RBF. The mixture was heated to 92.8° C., where upon a thick homogeneous mixture was observed. This was held at 92.8 to 95° C. for ~30 minutes, after which was cooled in an ice bath. At 85° C. a clear light yellow solution was observed, but was cooled to 2.8° C. The clarity of the solution was measure at 99.2 NTU (CAR-T-21-1). The concentrated solution was then diluted with water to 0.25 mg/mL and the clarity was measure at 3.14 NTU (CAR-T-21-2). After the concentrated solution (CAR-T-21-1) sat at room temperature overnight, a change in composition to a milky white solution was observed. This was then reheated and cooled to a clear solution, and a small sample was taken and placed in the refrigerator to monitor stability further. After a day in a vial, there was little to no fish smell, almost more of a TPGS smell.

Formulation using Ocean Technologies 90% Ethyl Ester with Stabilizers (Exp: CAR-T-23):

TPGS-1000 (23.3 g, Antares), Vitamin C (0.2 g), EDTA disodium (0.4 g), Vitamin C palmatate (0.5 g), Vitamin E (0.5 g), 90% ethyl ester high epa (70:10) (11.69 g, Organic Technologies) and water (81.8 g) were charged to a 250 mL 3-neck RBF. Note that bulk materials of 90% ethyl ester epa has a light fish smell. The mixture was heated to 94° C., where upon a thick homogeneous mixture was observed. This was held at 94-94.8° C. for ~30 minutes, after which was cooled in an ice bath. At 73° C. a clear light yellow solution was observed, but was cooled to 23° C. The clarity of the solution was measure at 28.1 NTU (CAR-T-23-2). The concentrated solution was then diluted with water to 0.22 mg/mL and the clarity was measure at 2.31 NTU (CAR-T-23-3). After the concentrated solution (CAR-T-21-1) sat at room temperature overnight, no change in composition was observed. Also, a small sample was placed in the refrigerator overnight with no change in composition observed. After a day in a vial, there was little to no fish smell, and almost ore of a TPGS smell.

Solubility, clarity and stability results of the solution prepared according to the procedures as described herein demonstrate that the formulations as described herein maintains clarity and stability for the desired period of time under the storage conditions.

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope.

What is claimed is:

1. A stable, water soluble formulation comprising:
   a) an omega-fatty acid;
   b) one or more solubilizing agents selected from the group consisting of Polysorbate 80, Polysorbate 20, Solutol HS 15, PEG-40 Hydrogenated castor oil (Cremophor RH40), PEG-35 Castor oil (Cremophor EL), or mixtures thereof; and
   c) a metal chelator and one or more than one additive selected from the group consisting of a water soluble reducing agent, a water soluble antioxidant, a water-insoluble reducing agent, a bisulfite salt, a metabisulfite salt or mixtures thereof;
   wherein the formulation is prepared by initially heating a mixture of the omega-fatty acid, the solubilizing agent, a metal chelator and one or more additives above 95° C., followed by cooling;
   wherein the formulation remains substantially clear and stable for a period of at least 6 months when stored at or below room temperature.

2. The water soluble formulation of claim 1, wherein the omega-fatty acid is selected from the group consisting of omega-3 fatty acid, omega-6 fatty acid, omega-9 fatty acid, omega-12 fatty acid, and mixtures thereof.

3. The water soluble formulation of claim 1, wherein the omega-fatty acid is selected from the group consisting of α-linolenic acid (ALA), stearidonic acid, eicosatetraenoic acid, eicosapentaenoic acid (EPA), docosapentaenoic acid, docosahexaenoic acid (DHA), linoleic acid, gamma-linolenic acid, eicosadienoic acid, dihomo-gamma-linolenic acid, arachidonic acid, docosadienoic acid, adrenic acid, docosapentaenoic acid, oleic acid, eicosenoic acid, mead acid, erucic acid and nervonic acid, and combinations thereof.

4. The water soluble formulation of claim 1, wherein the water-soluble or water-insoluble reducing agent and the water soluble antioxidant is selected from the group consisting of L-ascorbic acid-6-palmitate, vitamin C and its salts, alpha, beta, gamma, and delta tocopherol or mixtures of tocopherol, and alpha, beta, gamma, and delta-tocotrienols or mixtures thereof.

5. The water soluble formulation of claim 1, wherein the metal chelator is selected from the group consisting of ethylenediaminetetraacetic acid (EDTA), disodium EDTA and calcium disodium EDTA and mixtures thereof.

6. The water soluble formulation of claim 1, wherein the bisulfite is sodium bisulfite, potassium bisulfite, sodium metabisulfite or potassium metabisulfite.

7. The water soluble formulation of claim 1, wherein the formulation, when dissolved in water, provides a solution with a clarity range of about 1,000 to 20 NTU.

8. The water soluble formulation of claim 1, wherein the formulation, when dissolved in water, provides a solution that remains clear and stable toward degradation when stored at or below room temperature for a period of at least 6 months.

9. The water soluble formulation of claim 1, wherein the ratio of the solubilizing agent to omega-3 fatty acids is less than or equal to 2:1 to 0.5 to 1.

10. A method for stabilizing a substantially water insoluble lipophilic bioactive compound selected from the group consisting of omega-3 fatty acid, omega-6 fatty acid, omega-9 fatty acid, omega-12 fatty acid, and mixtures thereof, in an aqueous solution, the method comprising contacting the lipophilic bioactive compound with:
    a) a composition comprising one or more solubilizing agents selected from the group consisting of, Polysorbate 80, Polysorbate 20, Solutol HS 15, PEG-40 Hydrogenated castor oil (Cremophor RH40), PEG-35 Castor oil (Cremophor EL), or mixtures thereof; and
    b) a metal chelator and one or more additives selected from the group consisting of a water soluble reducing agent, a water-insoluble reducing agent, a bisulfite salt, a metabisulfite salt or mixtures thereof, for a sufficient period of time to dissolve the lipophilic bioactive compound;
    wherein the formulation is prepared by initially heating a mixture of the omega-fatty acid, the solubilizing agent, a metal chelator and one or more additives above 95° C., followed by cooling;
    wherein the resulting formulation remains substantially clear and stable for a period of at least 6 months when stored at or below room temperature.

11. The method of claim 10, wherein the dissolved aqueous composition provides a clear solution with a clarity range of about 1,000 to 20 NTU.

12. The method of claim 10, wherein the metal chelator is selected from the group consisting of ethylenediaminetetraacetic acid (EDTA), disodium EDTA and calcium disodium EDTA or mixtures thereof.

13. The stable water soluble formulation of claim 1, further comprising HI-CAP 100 (modified food starch derived from waxy maize), Emcap Starch (emulsifying starches), TICAMULSION FC (TIC GUMS, modified gum arabic) and Spray gum F (gum acacia with Maltrin-100 (maltodextrin)).

* * * * *